US008109905B2

(12) United States Patent
Saulenas et al.

(10) Patent No.: US 8,109,905 B2
(45) Date of Patent: *Feb. 7, 2012

(54) RETRACTABLE NEEDLE ASSEMBLY

(75) Inventors: William G. Saulenas, Wayne, NJ (US); Bradley M. Wilkinson, North Haledon, NJ (US); Volker Niermann, Bound Brook, NJ (US); Kirk D. Swenson, West Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 920 days.

This patent is subject to a terminal disclaimer.

(21) Appl. No.: 11/868,848

(22) Filed: Oct. 8, 2007

(65) Prior Publication Data

US 2008/0114296 A1    May 15, 2008

Related U.S. Application Data

(63) Continuation of application No. 10/279,190, filed on Oct. 23, 2002, now Pat. No. 7,294,118.

(60) Provisional application No. 60/399,318, filed on Jul. 26, 2002, provisional application No. 60/338,910, filed on Oct. 24, 2001.

(51) Int. Cl.
    *A61M 5/00*       (2006.01)
    *A61M 5/32*       (2006.01)

(52) U.S. Cl. ..................... 604/110; 604/177

(58) Field of Classification Search .............. 604/110, 604/192–198, 263, 181, 187, 171, 177, 158, 604/180, 164.01, 167.06, 165.01–165.03
See application file for complete search history.

(56) References Cited

U.S. PATENT DOCUMENTS

| 5,746,215 | A  | * | 5/1998 | Manjarrez ............. 600/573 |
| 5,779,679 | A  | * | 7/1998 | Shaw ..................... 604/158 |
| 6,540,732 | B1 | * | 4/2003 | Botich et al. ........... 604/413 |
| 6,786,875 | B2 | * | 9/2004 | Barker et al. ........... 600/585 |

FOREIGN PATENT DOCUMENTS

WO     WO 9111212    *  8/1991

* cited by examiner

*Primary Examiner* — Matthew F Desanto
(74) *Attorney, Agent, or Firm* — David M. Fortunato

(57) ABSTRACT

A fluid collection or infusion set is provided. The set includes flexible tubing with a fitting attached to a proximal end and a needle assembly attached to the distal end. The needle assembly includes a needle hub and a needle cannula secured in the hub. An actuator arm extends proximally and outwardly from the needle hub and has an actuator button at its free end. The needle assembly is disposed in a barrel and can move from a distal position where the needle cannula is exposed to a proximal position where the needle cannula is shielded. A spring is disposed in the barrel for propelling the needle assembly to the proximal position. The barrel includes an actuating aperture that receives the actuator button for locking the spring in a compressed condition. Depression of the actuator button enables the spring to propel the needle assembly into its proximal shielded position.

23 Claims, 23 Drawing Sheets

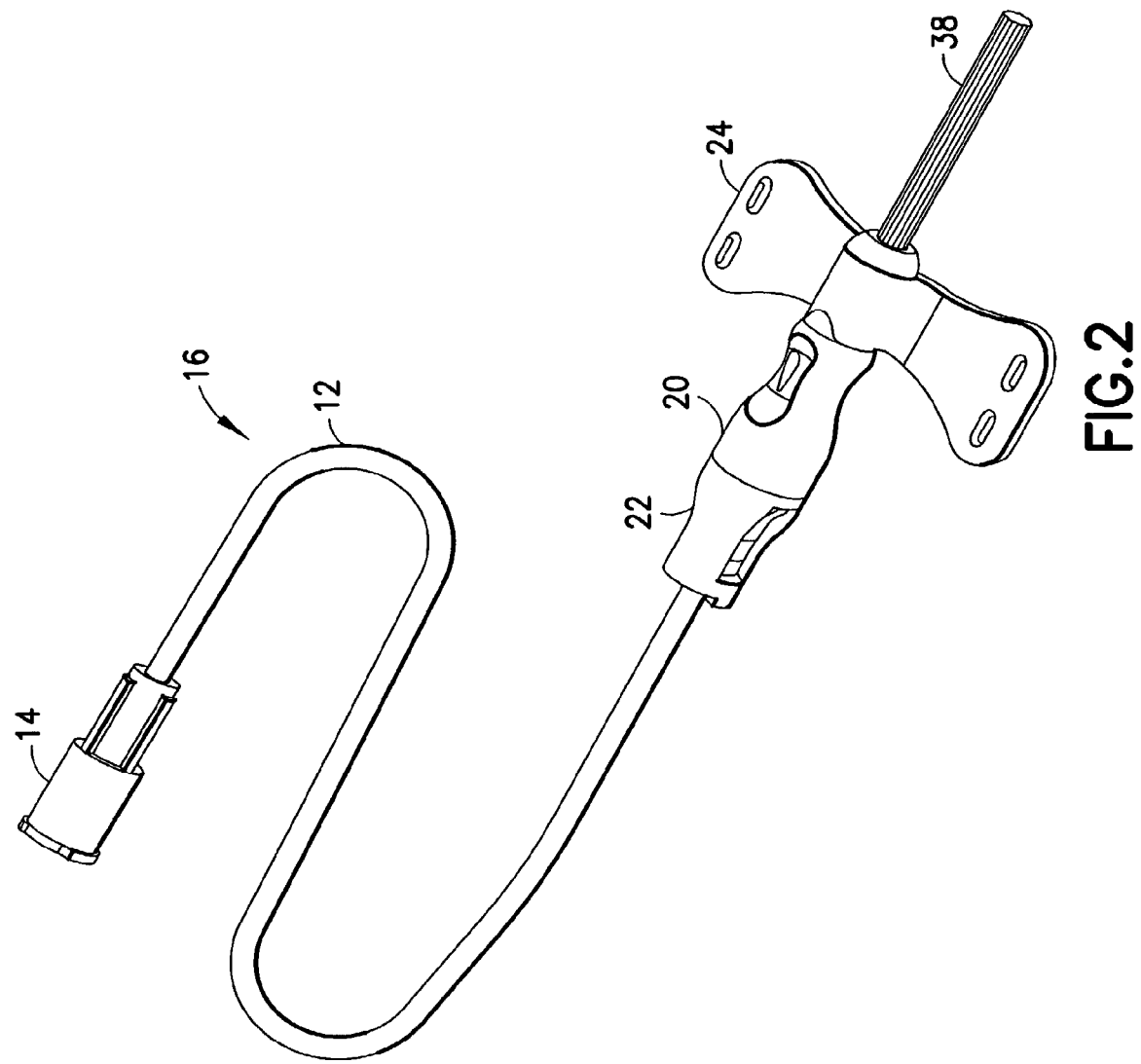

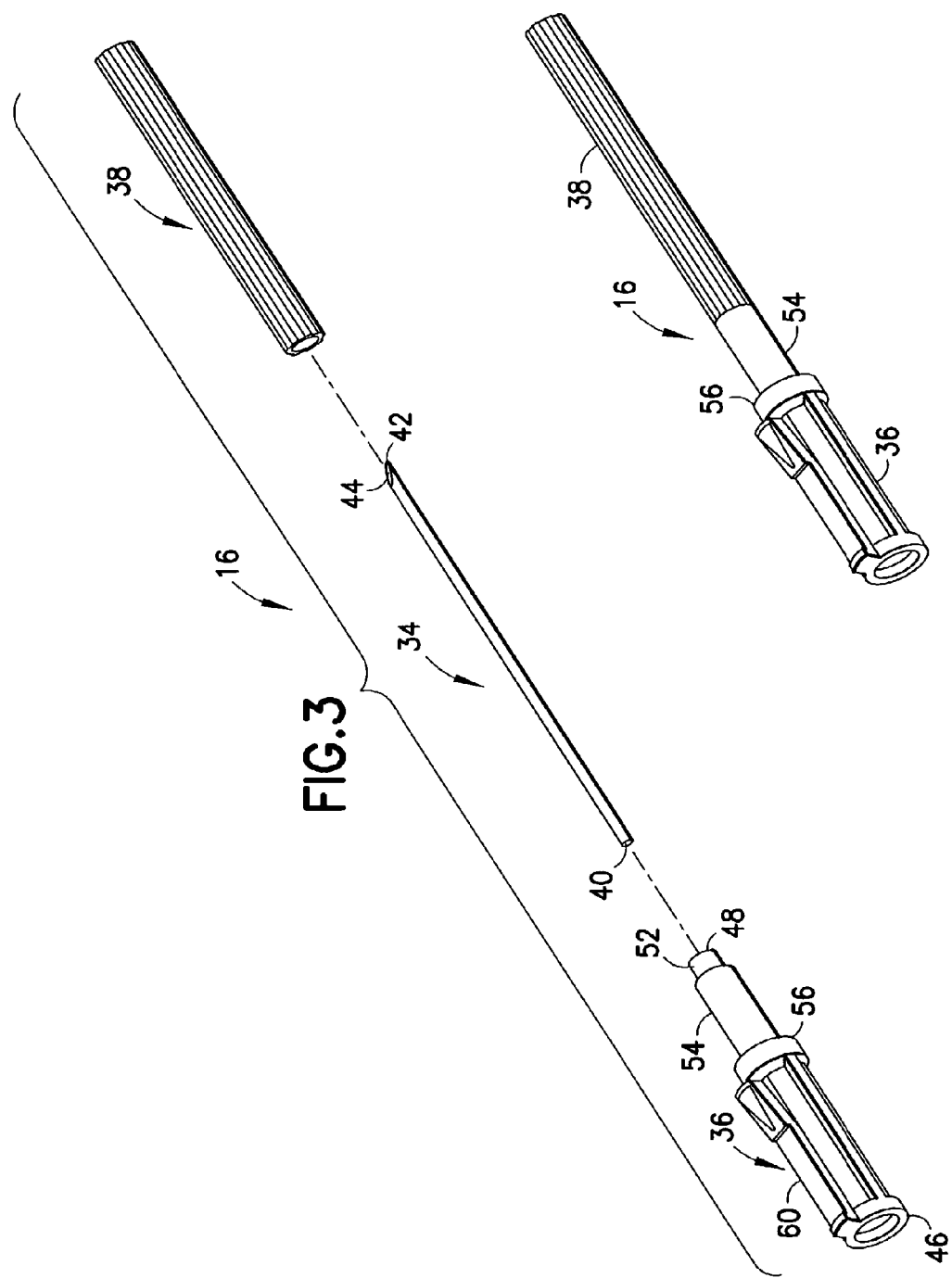

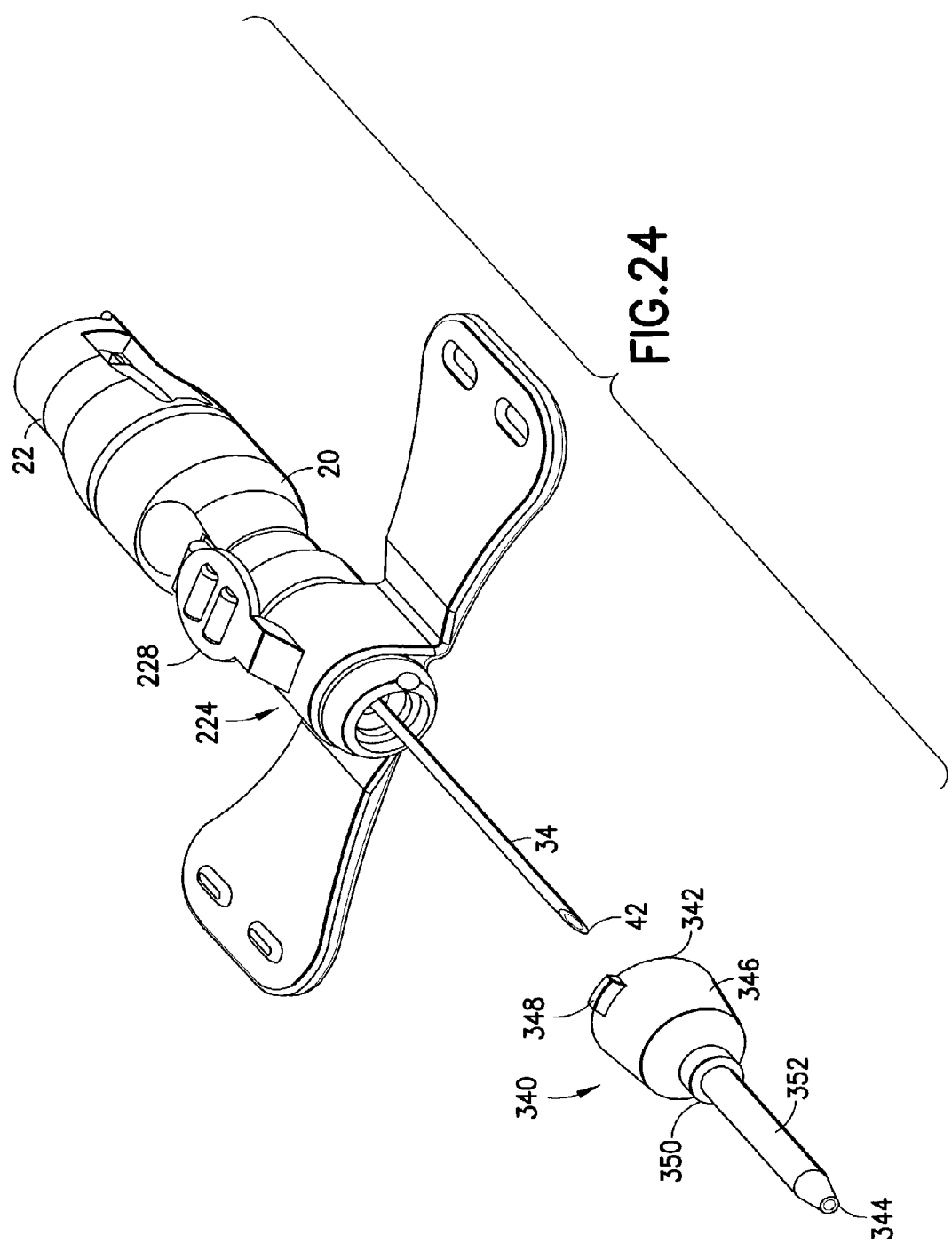

RETRACTABLE NEEDLE ASSEMBLY

CROSS-REFERENCE TO RELATED APPLICATIONS

The present application is a continuation of U.S. patent application Ser. No. 10/279,190 filed Oct. 23, 2002, which claims priority to U.S. patent application Ser. No. 60/399,318 filed Jul. 26, 2002 and U.S. patent application Ser. No. 60/338,910 filed Oct. 24, 2001.

FIELD OF THE INVENTION

The invention relates to a medical apparatus with a piercing element.

BACKGROUND OF THE INVENTION

Fluid collection sets, intravenous infusion sets and catheters are employed respectively for collecting bodily fluids from a patient, for infusing liquids into a patient. Fluid collection sets and intravenous infusion sets include a length of flexible plastic tubing with a proximal end connected to a plastic fitting and a distal end connected to a needle assembly. The needle assembly includes a hub and needle cannula. A pair of flexible plastic wings is mounted to or near the hub. The wings can be folded into face-to-face engagement with one another, and hence define a convenient handle for gripping and manipulating the needle cannula. The wings also can be rotated away from one another and can be taped into face-to-face contact with the skin of the patient. A catheter typically is used with an elongate piercing element for introducing the catheter into a patent.

Accidental sticks with a needle cannula can be painful and can transmit disease. As a result, most needle assemblies and other sharp medical implements are employed with rigid means for enclosing at least the sharp tip both prior to use and after use. Protection prior to use typically is achieved by a rigid plastic tube that has a proximal end frictionally mounted to or near the hub and a distal end that extends beyond the distal end of the piercing element. The plastic tube is removed and discarded immediately prior to use of the piercing element. Protection after use typically is achieved by a tubular shield that can be telescoped relative to both the hub and piercing element from a proximal position where the piercing element is exposed to a distal position where the piercing element is safely within the tubular shield. Shields of this type typically include means for releasably holding the shield in its proximal position and for holding the shield more securely in its distal position. Some devices include a spring for generating relative movement between the shield and the piercing element. In some instances, the shield is moved distally over the piercing element. In other instances, the piercing element is withdrawn proximally into the shield.

A small volume of blood or other bodily fluid may remain in or on a piercing element after the piercing element has been withdrawn from the patient. This residual fluid may splatter as the piercing element is retracted rearwardly into a shield. The probability of such splatter from a needle is dependent upon several factors, including the gauge of the needle, the acceleration of the needle in the proximal direction, the presence of any transverse movement of the needle during its rearward acceleration, the extent of capillary adhesion of the residual fluid on portions of the cannula that define the lumen and other factors. Splatter of bodily fluid can transmit disease.

Health care workers are required to use many different medical devices, and often use medical devices from several different manufacturers. The configuration and operation of the shields on the above-described medical devices vary widely from one manufacturer to another. A lack of familiarity with the specified operation of a shield for a particular medical device can lead to improper shielding and hence creates the potential for an accidental stick with a used needle cannula.

The ease of shielding and the effectiveness of the shielding also vary from one type of medical device to another. Devices that are mechanically simple may provide less effective shielding. More secure shielding may require more complex manipulation of the device by the health care worker. In view of the above, a demand exists for a medical device that provides secure shielding and an easy operation.

SUMMARY OF THE INVENTION

The present invention is a medical apparatus with a retractable piercing element. The apparatus may be a fluid collection or infusion set that comprises a length of flexible tubing with opposite proximal and distal ends and a passage extending between the ends. A fitting is secured to the proximal end of the flexible tubing and a needle assembly is secured to the distal end of the flexible tubing.

The piercing element may be a needle cannula having opposite proximal and distal ends and a lumen extending between the ends. The apparatus may include a hub with a proximal end, a distal end and a passage extending between the ends. A resiliently deflectable actuator arm is cantilevered from the hub and the free end of the cantilevered actuator arm is formed with an outwardly projecting actuator button. The proximal end of the piercing element is affixed to distal portions of the hub. Thus, a lumen that may be provided in the piercing element may communicate with the passage through the hub and with the passage through the flexible tubing. A rigid protector may be mounted removably over the piercing element and may extend sufficiently to cover the distal end of the piercing element.

The apparatus further includes a barrel telescoped over the hub such that the piercing element is movable relative to the barrel from a distal position to a proximal position. More particularly, the pointed distal end of the piercing element projects distally beyond the barrel when the piercing element is in the distal position relative to the barrel. However, all of the piercing element is safety enclosed within the barrel when the piercing element is in the proximal position relative to the barrel.

The barrel includes an actuation region that has an actuating aperture disposed and configured to permit engagement of the actuator button when the piercing element is in the distal position. Portions of the actuating region of the barrel may define a smaller cross-section than portions of the barrel either distally or proximally of the actuating region. Thus, the actuating aperture and the actuator button are recessed slightly relative to portions of the barrel on either longitudinal side of the actuating region to prevent inadvertent actuation that could displace the needle assembly relative to the barrel. Additionally, the recessed shape of the actuator region provides a visual cue to identify regions of the barrel that should be digitally accessed to retract the piercing element. This allows the user to locate the actuator button during use with or without visually seeing it and sometimes only relying on the change in tactile surface near the actuator region. The exterior shape of the barrel is preferably circular when viewed in a cross section perpendicular to the barrel's axis.

The barrel comprises means for preventing re-exposure of the piercing element after shielding has been effected. For example, the barrel may include an array of inwardly directed resilient fingers aligned to permit retraction of the piercing element relative to the barrel, but to prevent re-exposure of the retracted piercing element.

The apparatus further includes a pair of flexible wings. The wings preferably are formed separately from the barrel and are securely mounted to a portion of the barrel near the actuating region. Thus, the barrel may be formed from a first material selected for rigidity, while the wings may be formed from a second material selected for flexibility.

A lever may also be located on the barrel or in conjunction with the wings and in relation to the actuator button so as to activate the retractable piercing element.

The retractable apparatus further includes a spring for propelling the piercing element and hub proximally relative to the barrel. The spring may be biased to a collapsed condition when the piercing element is in its distal position relative to the barrel. However, disengagement of the actuator button from the actuating window permits the spring to expand and propels the piercing element and hub into its proximal position relative to the barrel.

The hub and barrel of the apparatus preferably are formed from translucent or transparent materials to provide "venous indication" or "flash" when the apparatus is part of a fluid collection set. This allows the user to identify when venous blood has reached the fluid path proximal from the proximal end of the needle cannula and to identify when venous blood has reached the inside of the needle hub.

The apparatus may further include a dampening agent, such as a viscous or non-viscous dampening agent to alter the acceleration and velocity of piercing element. Viscous dampening agents include grease, oil, gel, gel resin, or any combination thereof and non-viscous dampening agents include biased flexible elements extending between the front and rear barrels or the needle hub. Preferably, the dampening agent is a material with an ability to temporarily elastically bond the coils of the spring together. Thus, when retraction is initiated by pushing the actuator button, the bond between adjacent coils achieved by the dampening agent slows the initial opening of the coils from the tightly compressed state of the spring in the collapsed condition. As a result, the dampening agent preferably provides a slower initial acceleration and hence reduces splatter.

The apparatus may be used with a catheter telescoped over the piercing element and frictionally retained on the hub or barrel.

The retractable apparatus is packaged with the piercing element in a distal position relative to the barrel. The packaging preferably is configured to prevent inadvertent actuation. The apparatus then is removed from its packaging for use. Use commences by folding the wings into face-to-face engagement with one another and holding the folded wings between a thumb and forefinger. The health care worker then pulls the protector from the apparatus to expose the distal end of the piercing element. The distal end of the piercing element then is guided into a blood vessel or other targeted location. The fitting that may be provided at the proximal end of the tubing may be placed in communication with a source or reservoir for fluid in those instances where the apparatus is part of a fluid collection set or an infusion set. The ordering of these steps may vary depending on whether the set is used for fluid collection or for infusion. Upon completion of the medical procedure, the health care worker merely depresses the actuator button. The depression of the actuator button releases the actuator button from the actuating aperture and permits the spring to propel the piercing element proximally and into the shielded position within the barrel. The locking structure on the barrel prevents complete proximal separation of the piercing element from the barrel and prevents re-exposure of the used piercing element.

BRIEF DESCRIPTION OF THE DRAWINGS

FIG. 2 is a perspective view of the fluid collection set in its assembled condition.

FIG. 3 is an exploded perspective view of the needle assembly.

FIG. 4 is a perspective view of the needle assembly in its assembled condition.

FIG. 24 is an exploded perspective view showing the piercing element prior to retraction, but after separation from the catheter.

DETAILED DESCRIPTION OF THE INVENTION

Figure 1:
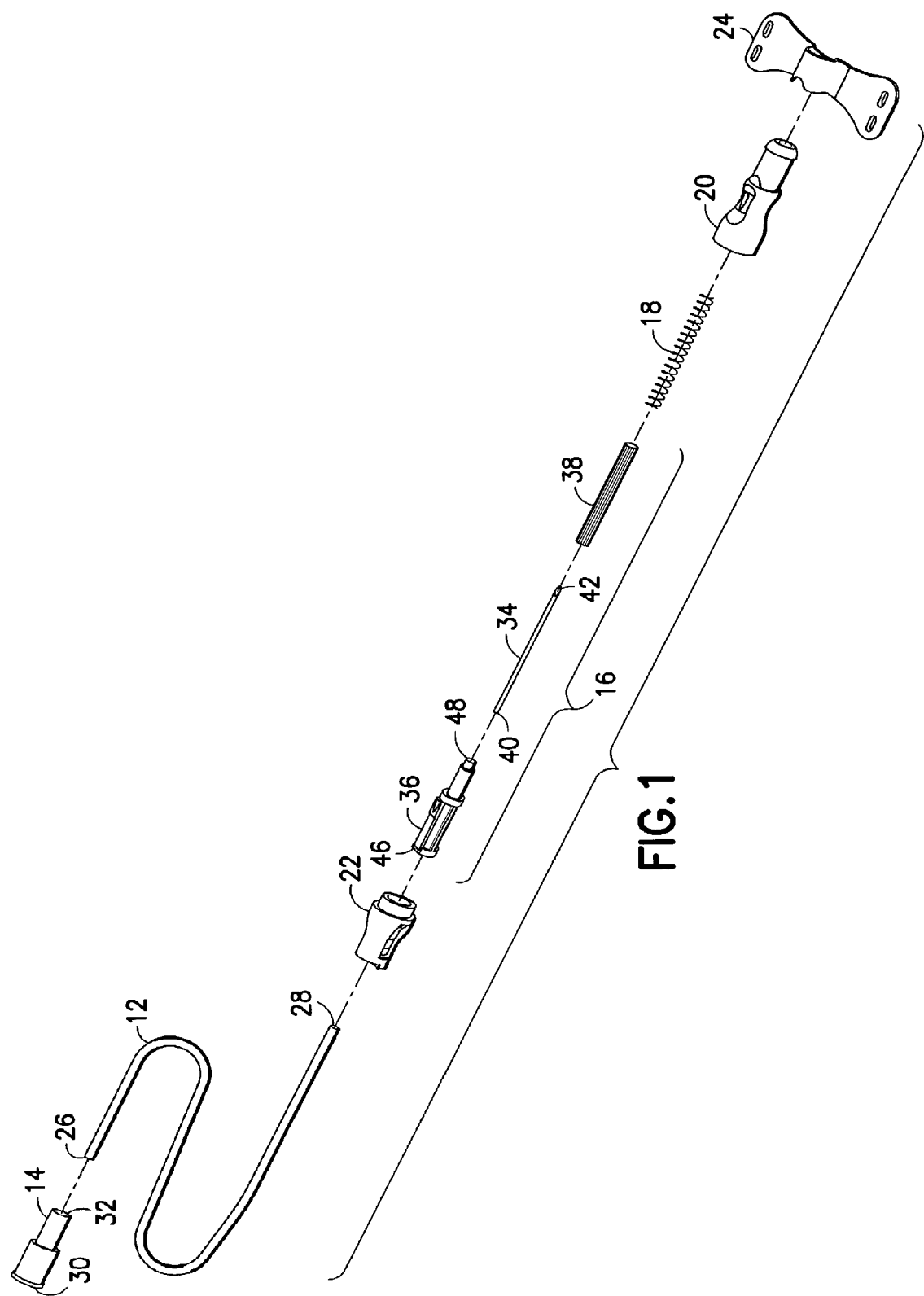
FIG. 1 is an exploded perspective view of a fluid collection or infusion set in accordance with the invention.
Figure 5:
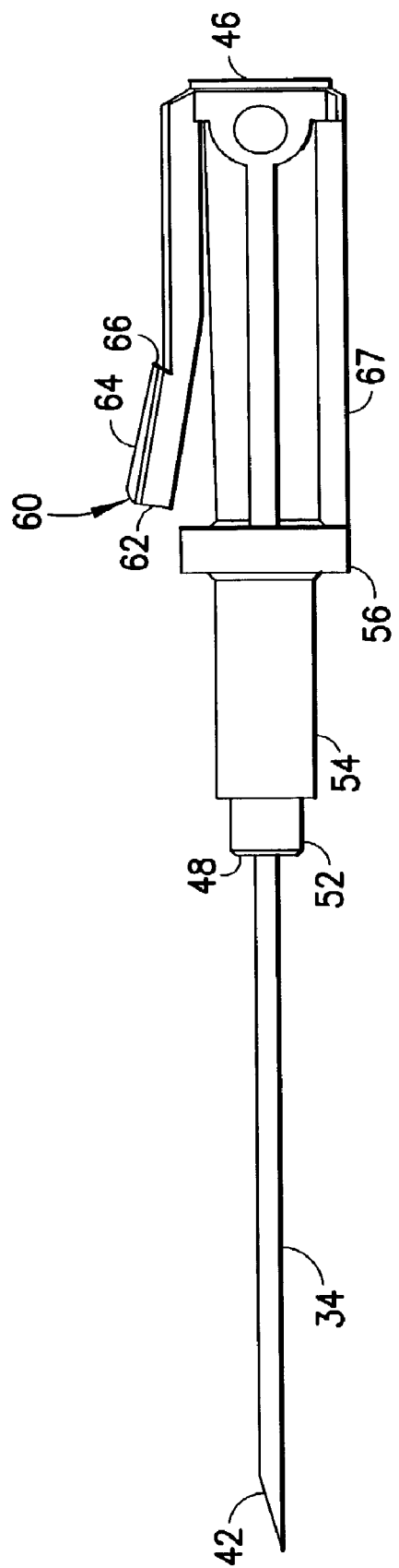
FIG. 5 is a side elevational view of the needle assembly.
Figure 6:
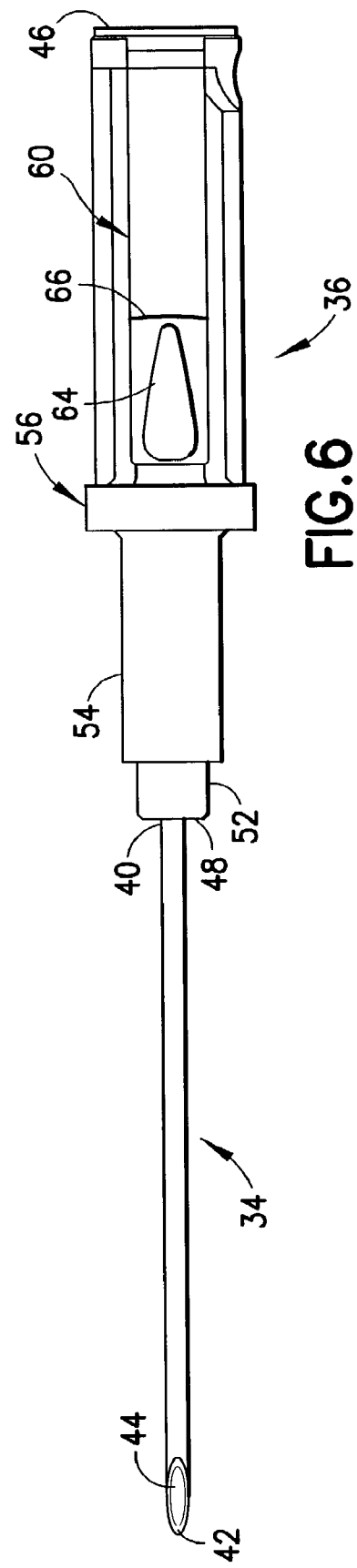
FIG. 6 is a top plan view of the needle assembly.
Figure 7:
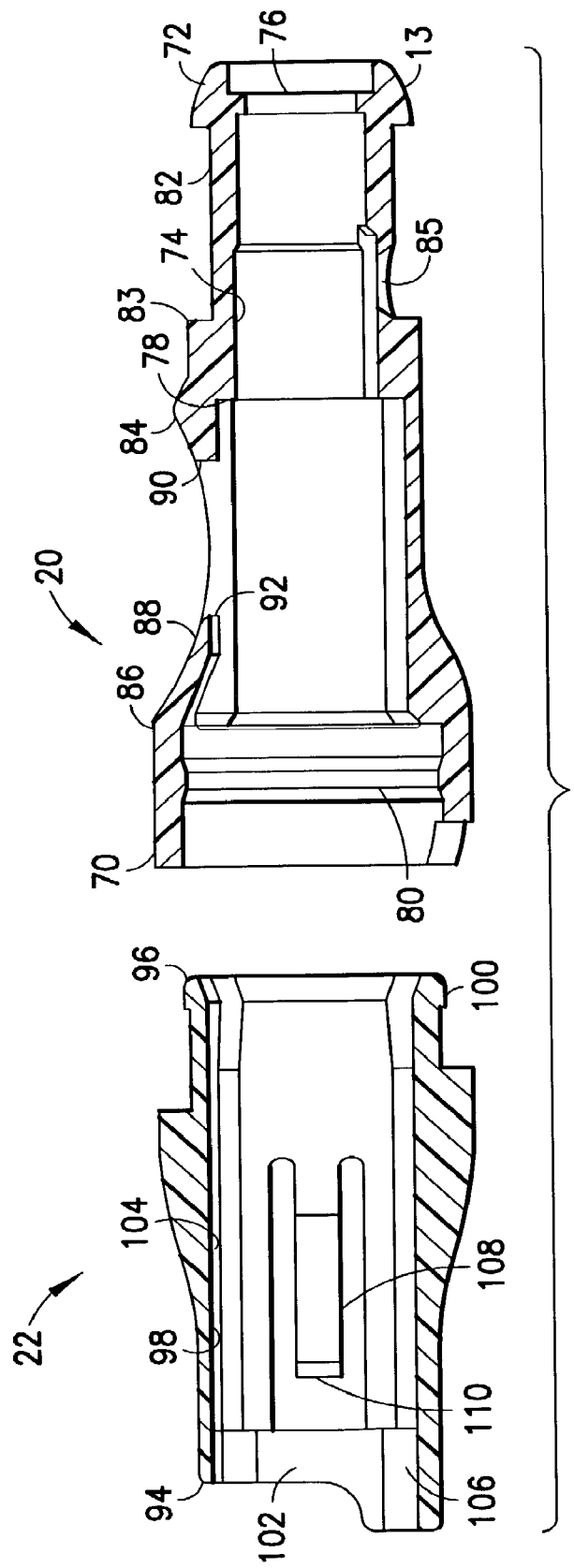
FIG. 7 is an exploded cross-sectional view of the barrel.
Figure 8:
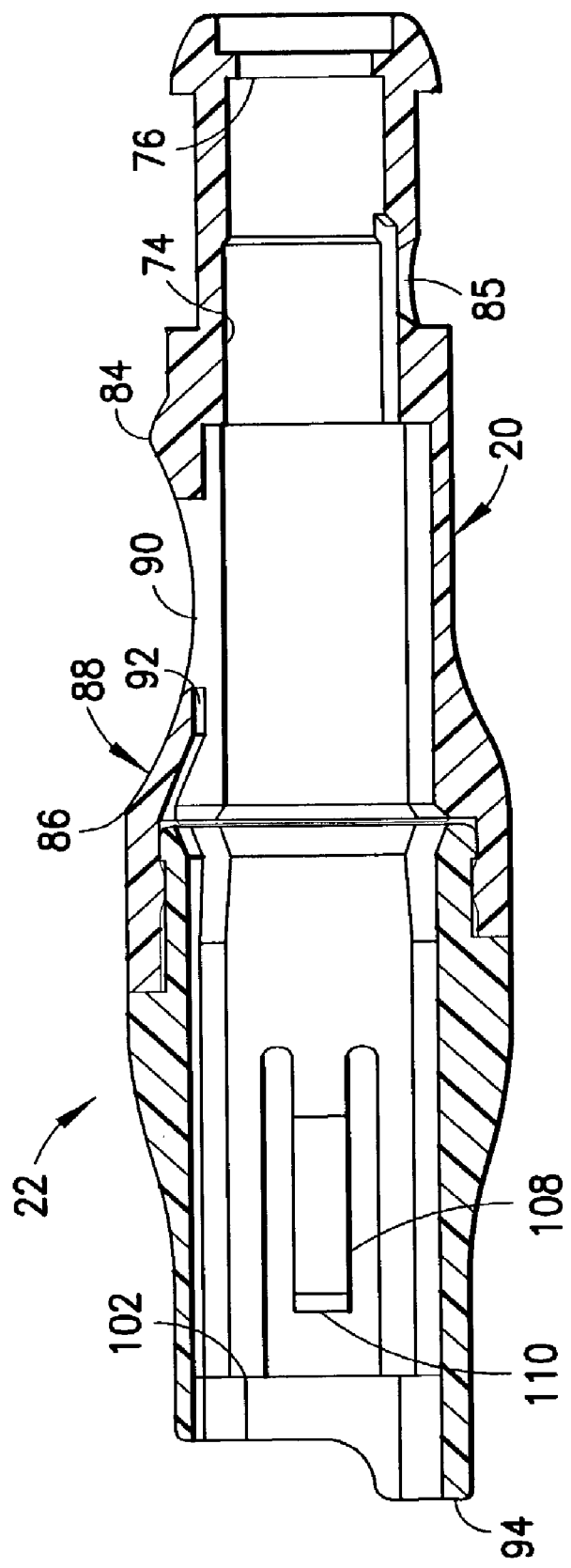
FIG. 8 is a longitudinal cross-sectional view of the barrel in its assembled condition.
Figure 9:
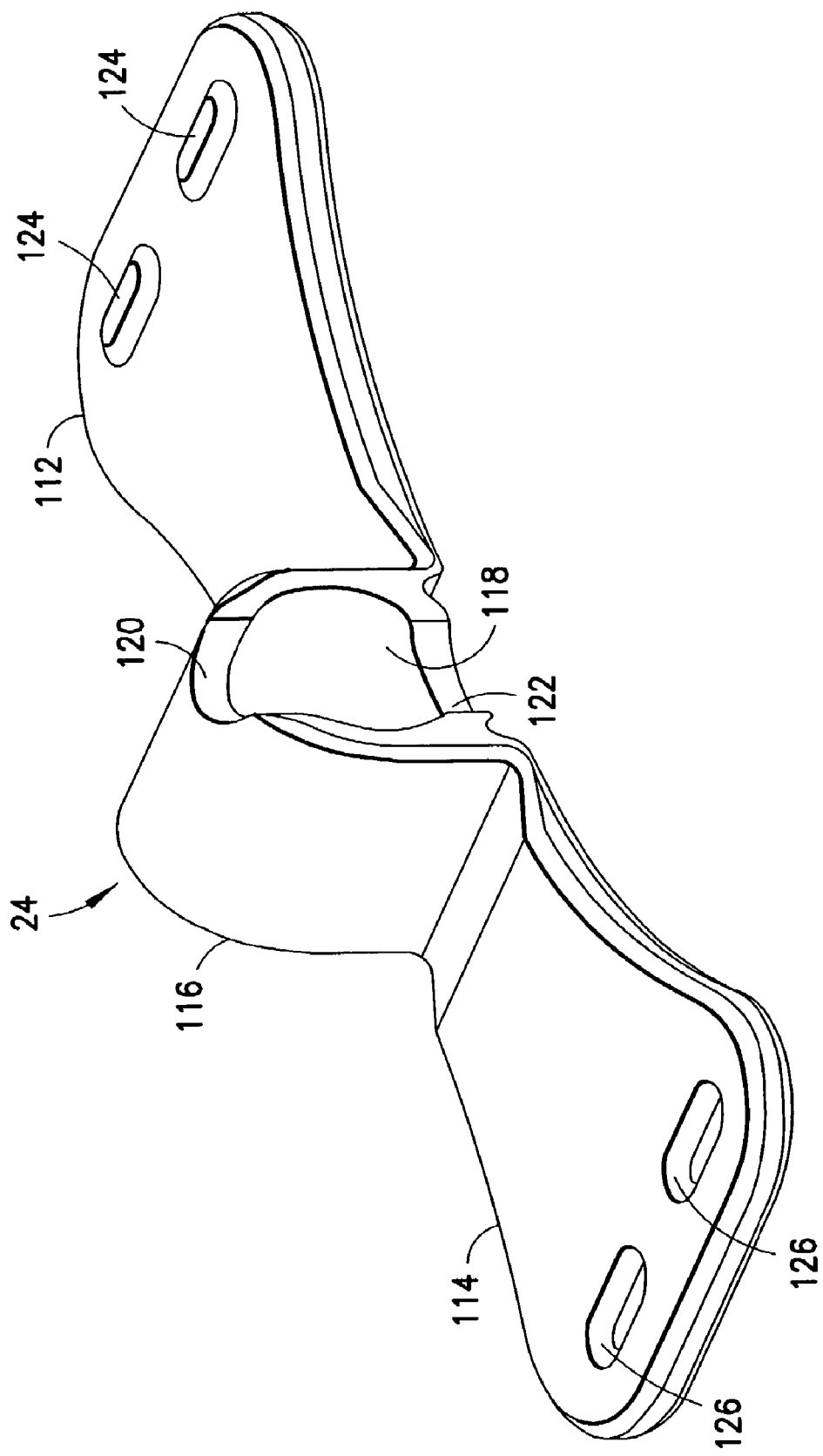
FIG. 9 is a perspective view of one embodiment of the wings.
Figure 10:
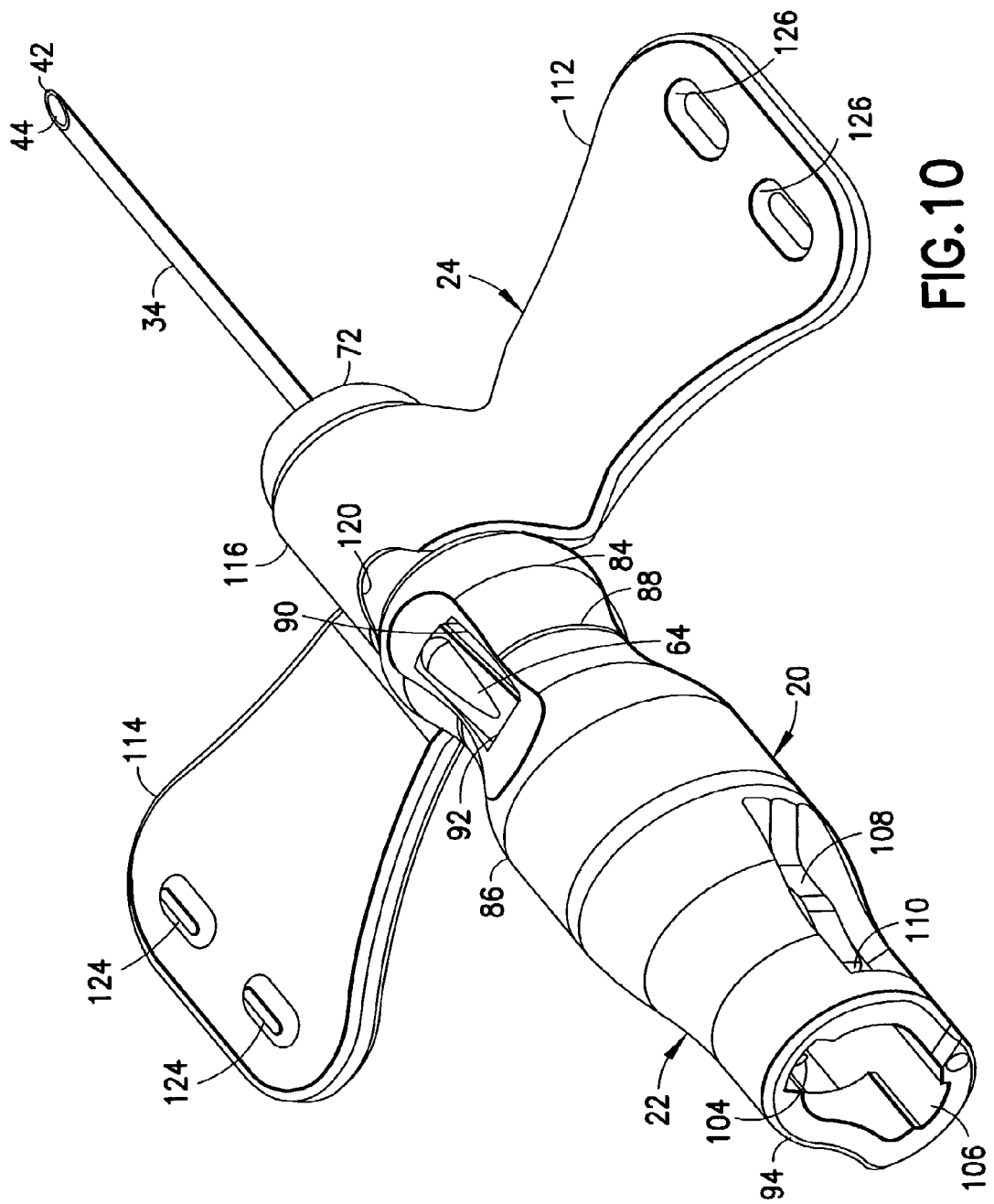
FIG. 10 is a perspective view of the retractable needle apparatus of the fluid collection set with the needle assembly in its distal position.
Figure 11:
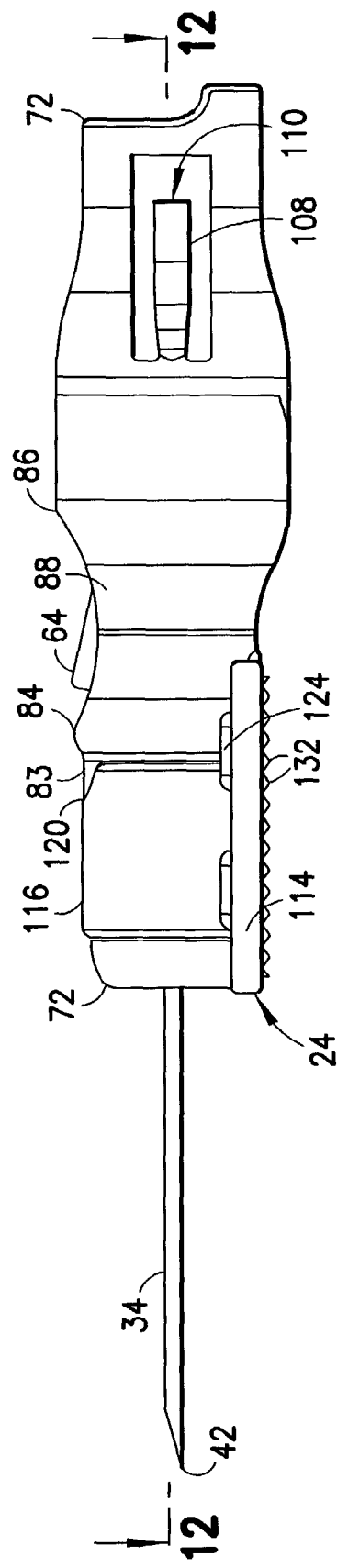
FIG. 11 is a side elevational view of the retractable needle apparatus shown in FIG. 10.
Figure 12:
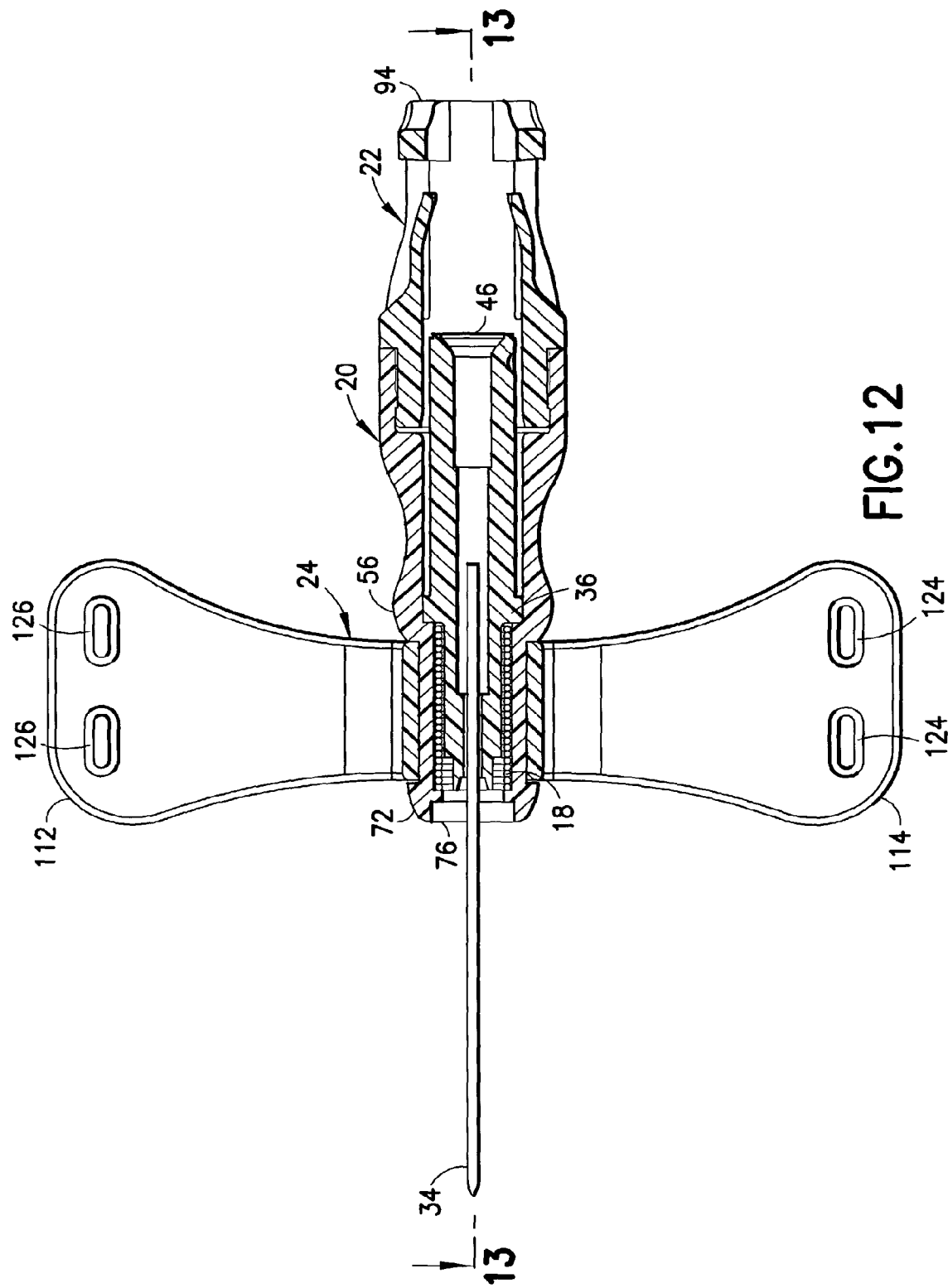
FIG. 12 is a cross-sectional view taken along line 12-12 in FIG. 1.
Figure 13:
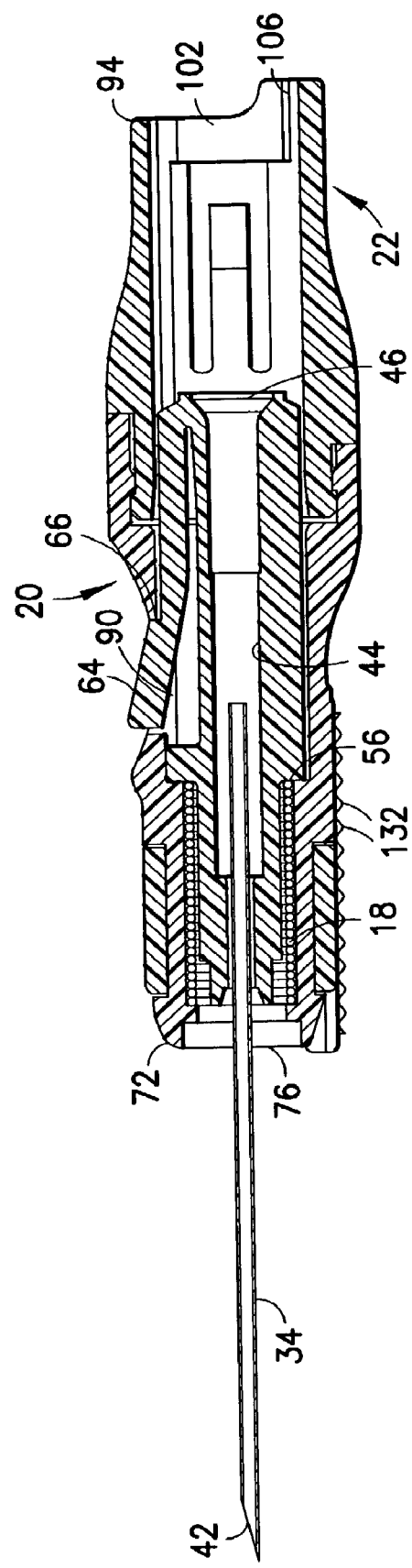
FIG. 13 is a cross-sectional view taken along line 13-13 in FIG. 12.
Figure 14:
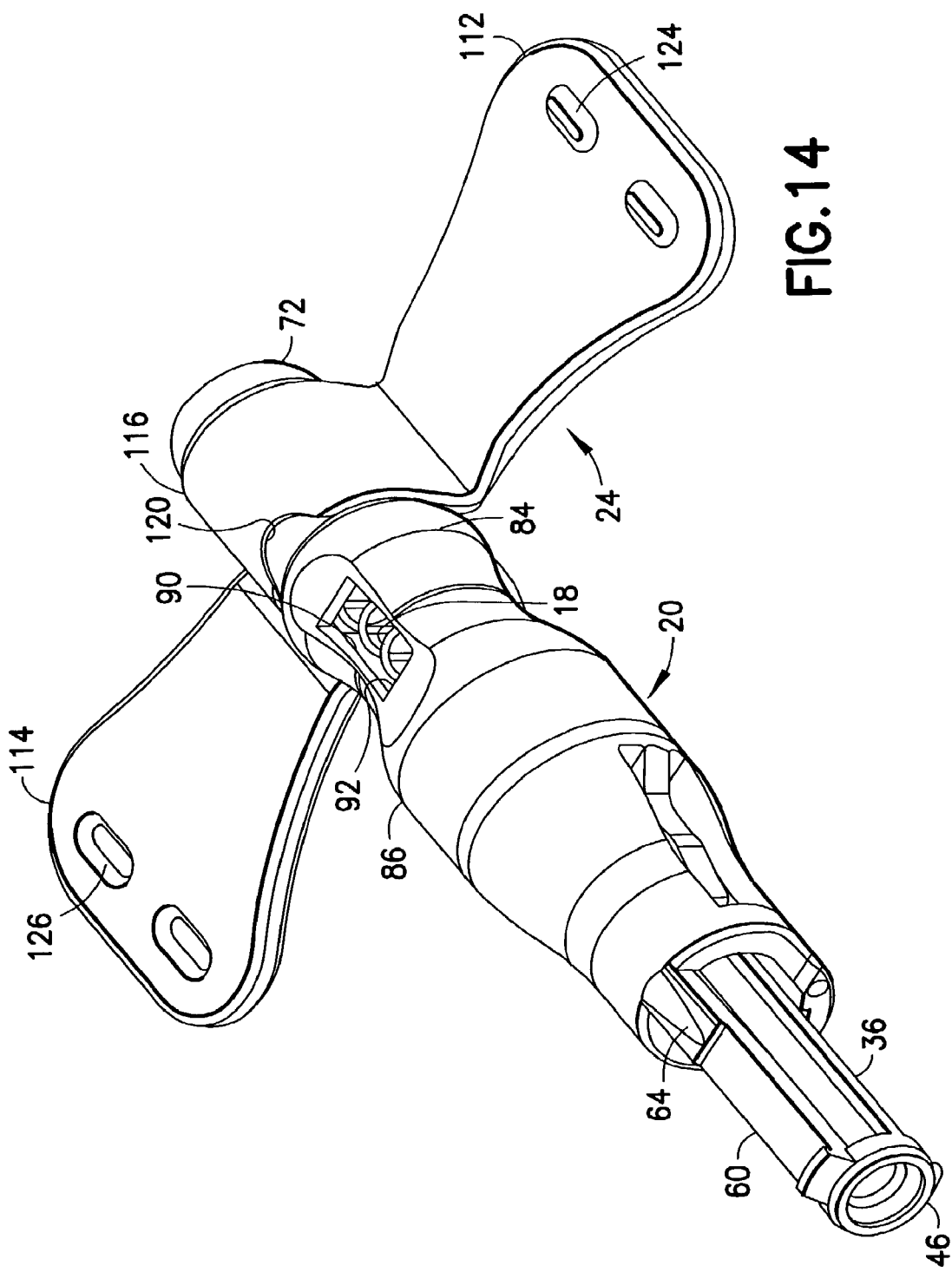
FIG. 14 is a perspective view similar to FIG. 10, but showing the needle assembly in the retracted position.
Figure 15:
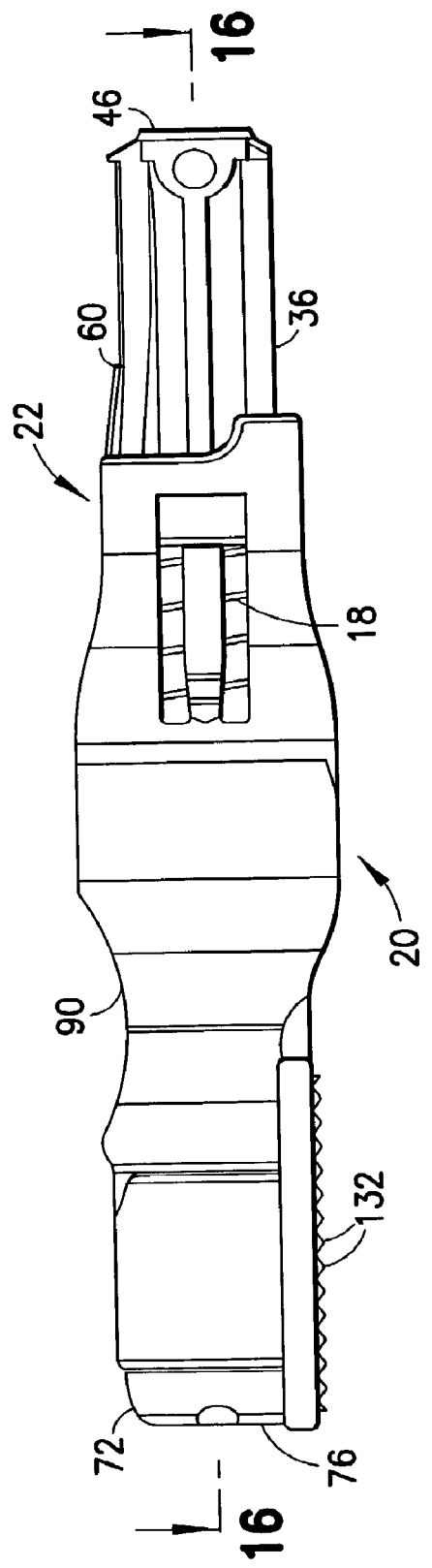
FIG. 15 is a side elevational view similar to FIG. 11 but showing the needle assembly in the retracted position.
Figure 16:
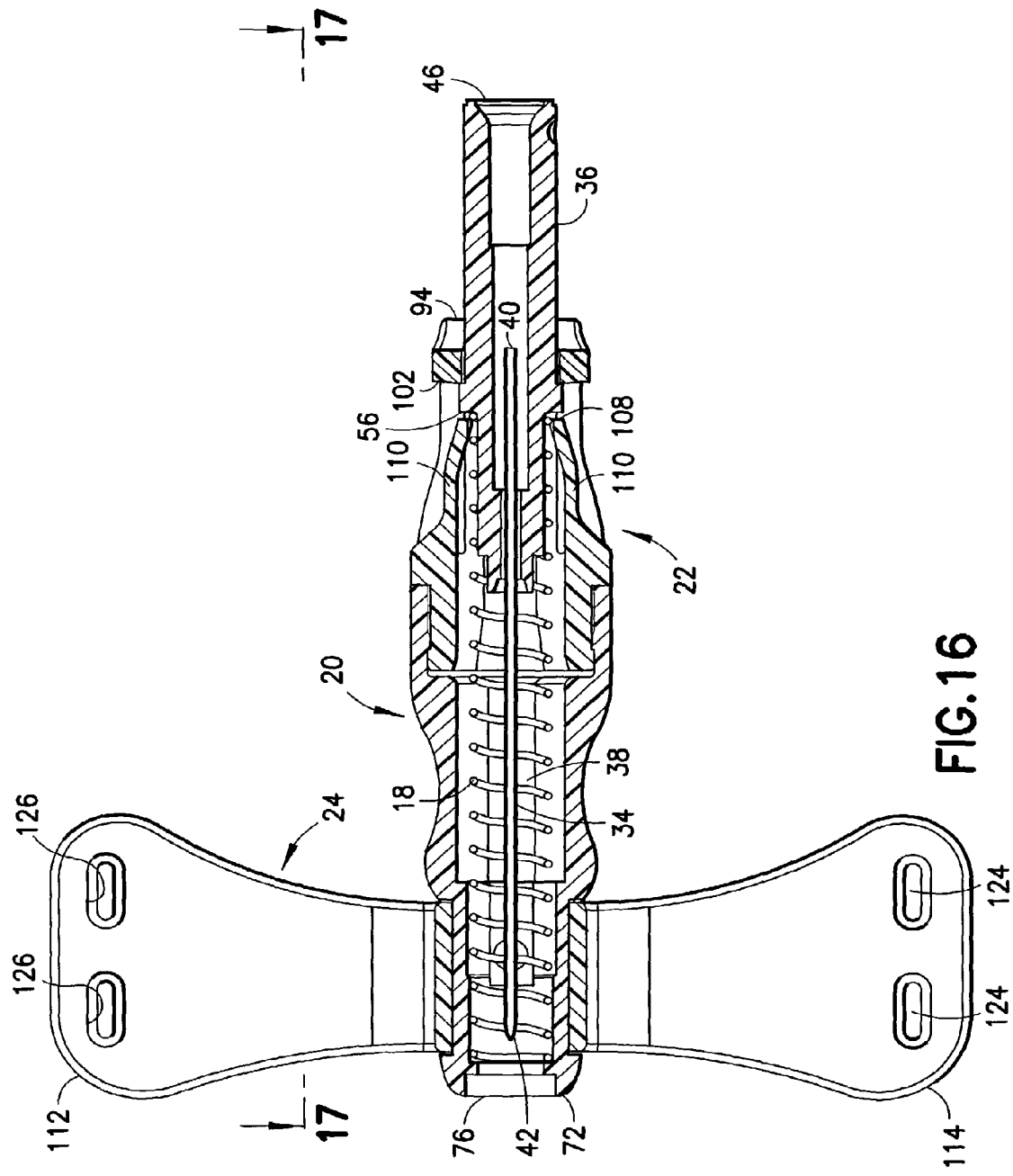
FIG. 16 is a cross-sectional view taken along line 16-16 in FIG. 15.
Figure 17:
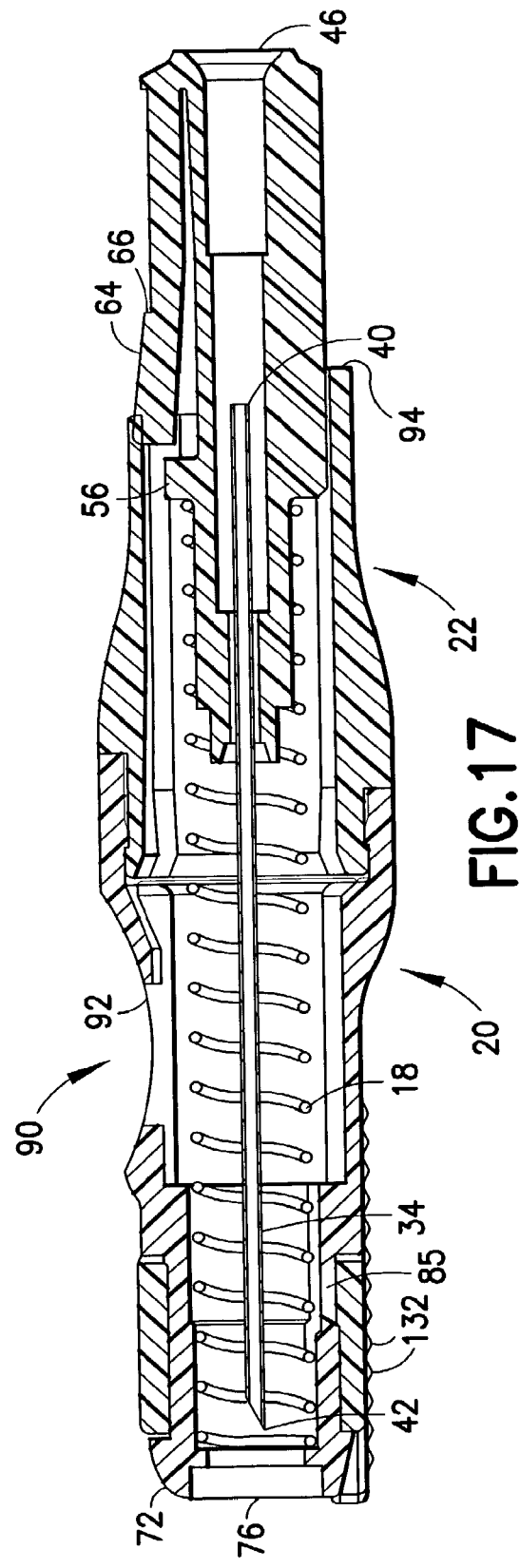
FIG. 17 is a cross-sectional view taken along line 17-17 in FIG. 16.
Figure 18:
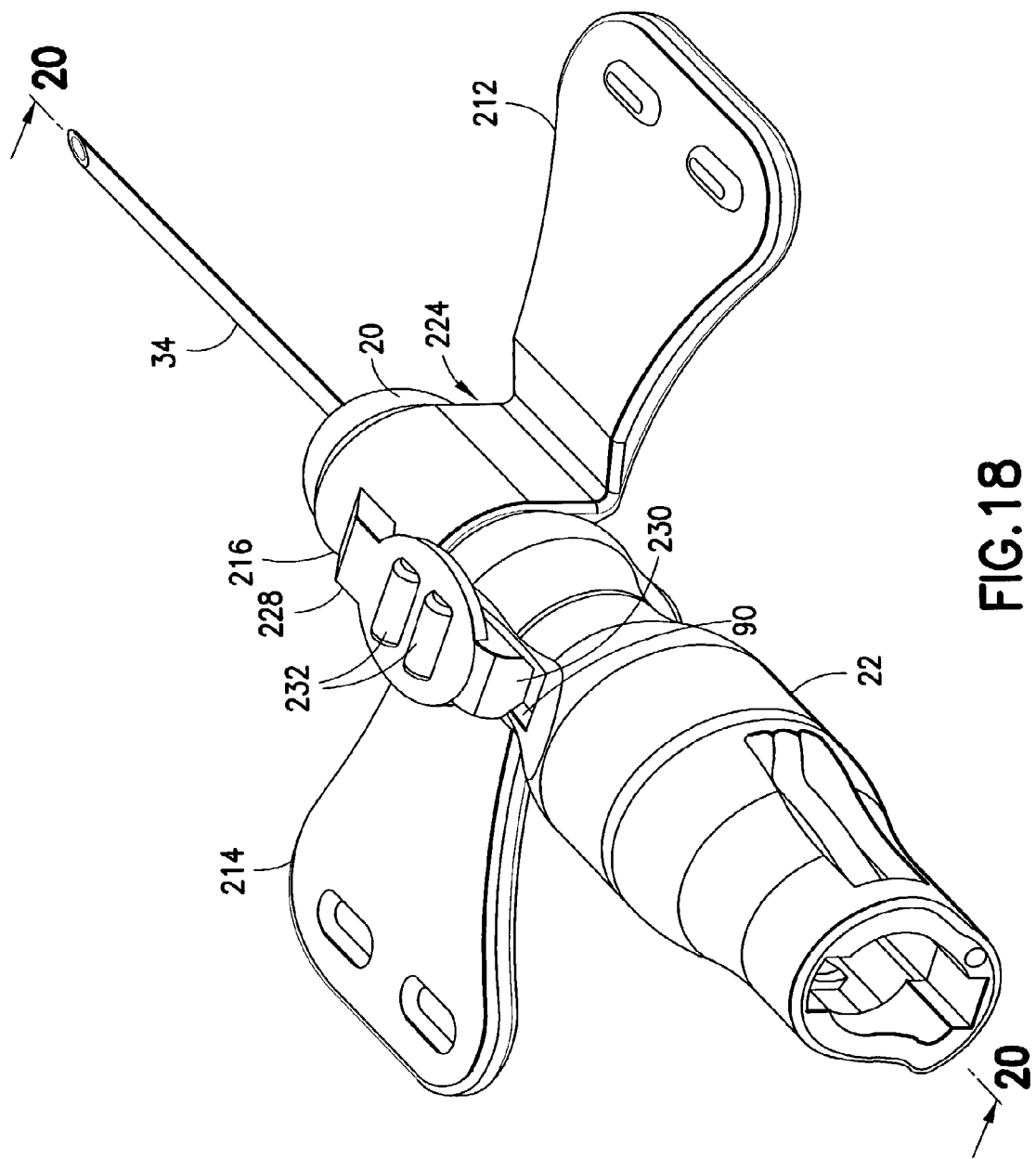
FIG. 18 is a perspective view similar to FIG. 10, but showing an additional embodiment of the wings.
Figure 19:
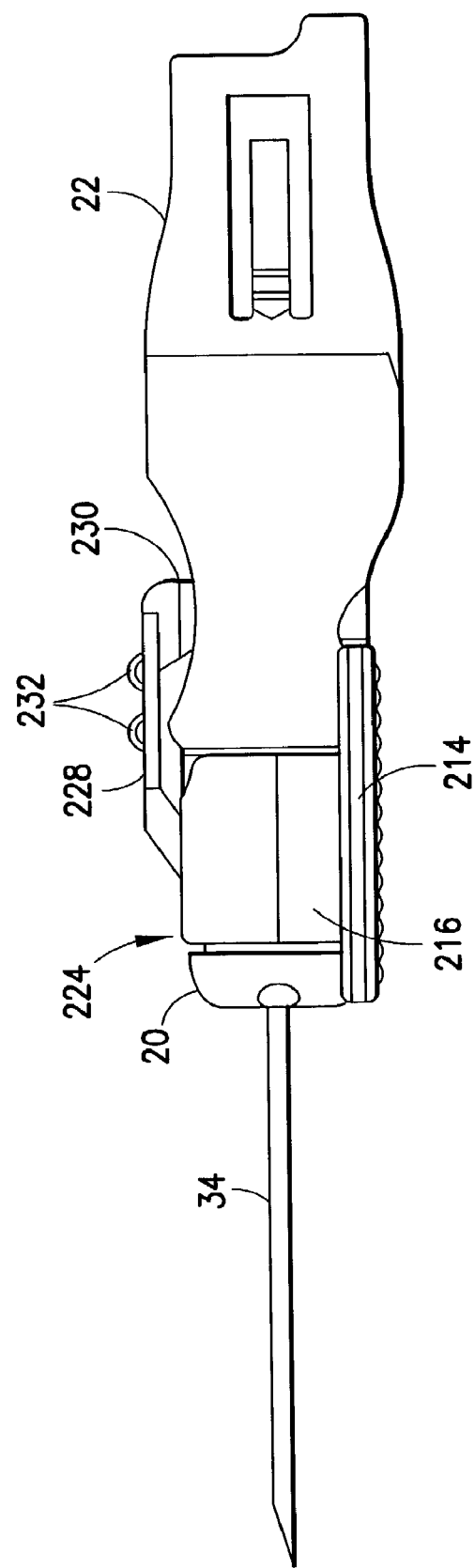
FIG. 19 is a side elevational view of the embodiment in FIG. 18.
Figure 20:
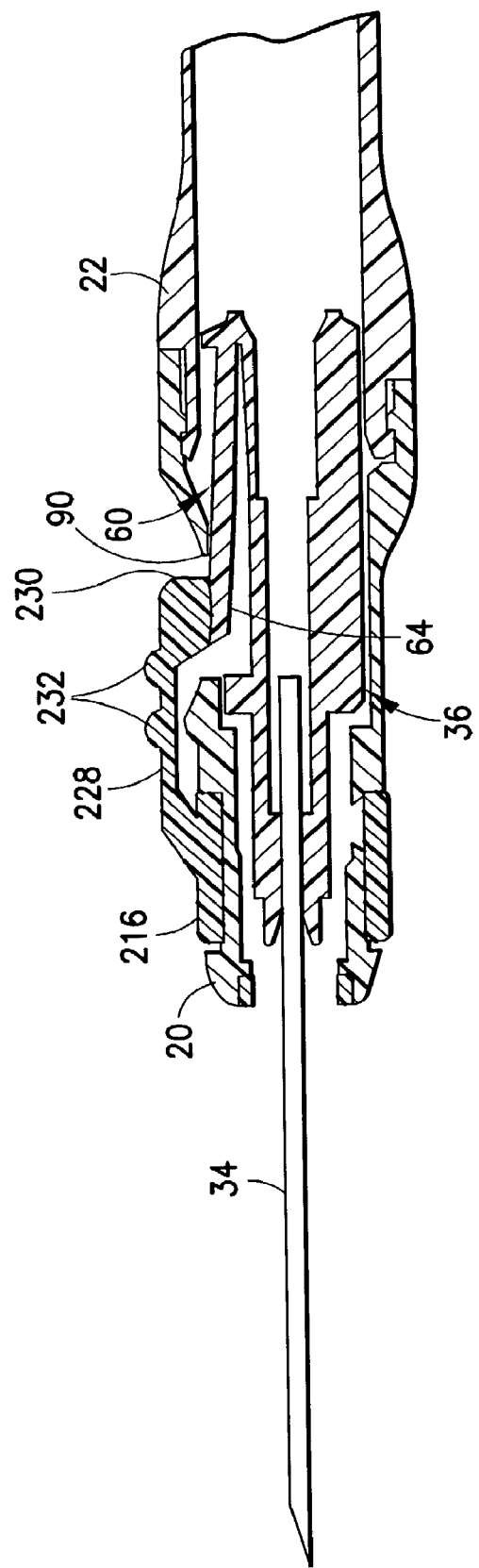
FIG. 20 is a cross-sectional view taken along line 20-20 in FIG. 18.
Figure 21:
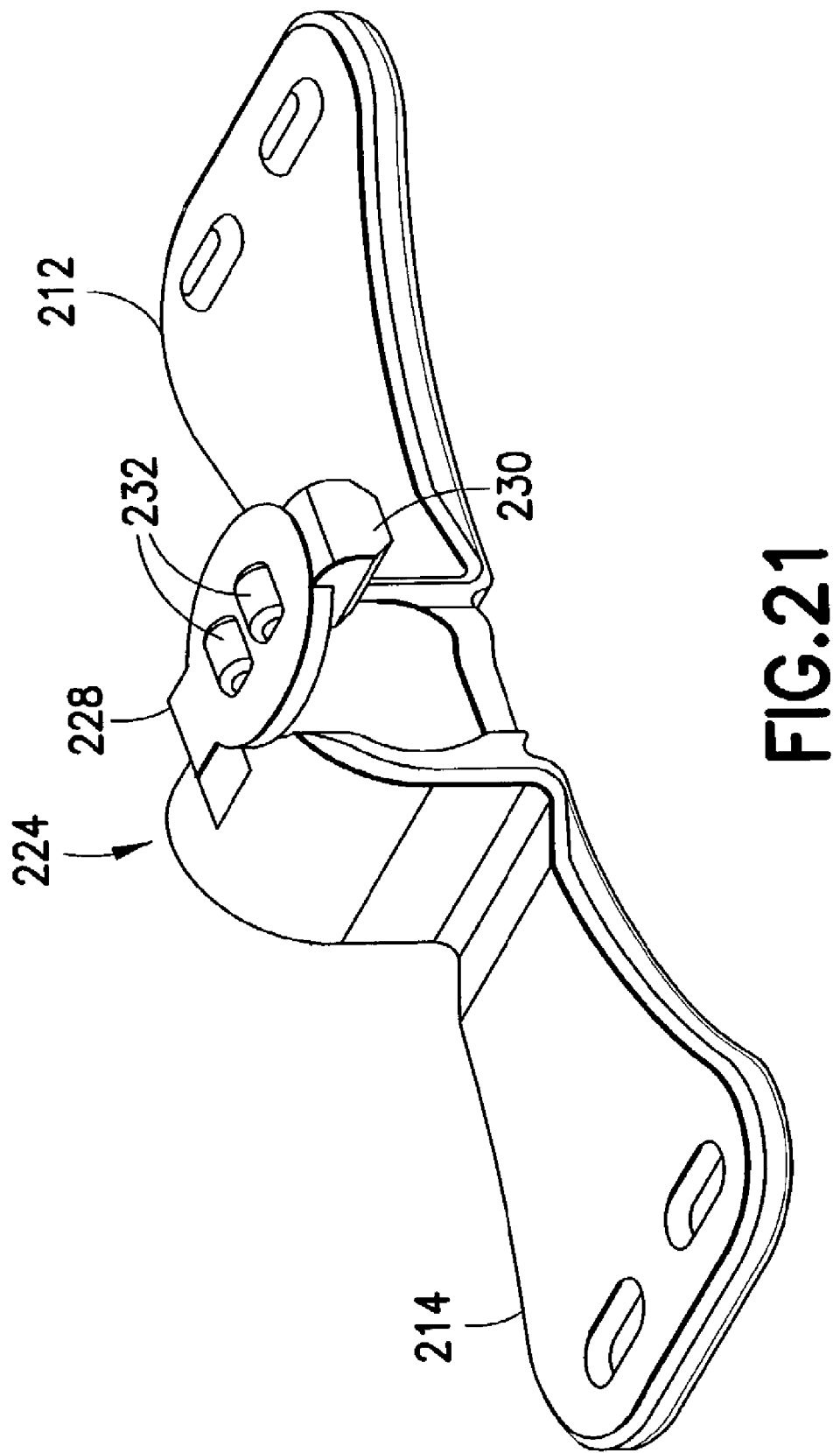
FIG. 21 is a side elevational view of the wings shown in FIGS. 18-20.

A fluid collection/infusion set in accordance with the subject invention is identified generally by the numeral 10 in FIGS. 1-3. Fluid collection/infusion set 10 includes a length of flexible plastic tubing 12, a proximal fitting 14, a needle assembly 16, a spring 18 and a barrel assembly that comprises a front barrel 20, a rear barrel 22 and a wing 24.

Tubing 12 includes a proximal end 26, a distal end 28 and a passage extending between the ends. Tubing 12 may be conventional intravenous tubing used in conventional blood collection sets or infusion sets.

Proximal fitting 14 is molded unitarily from a plastic material and includes a proximal end 30, a distal end 32 and a passage extending between the ends. Portions of the passage adjacent distal end 32 are configured to telescope tightly over proximal end 26 of tubing 12 so that the passage through tubing 12 communicates with the passage through connector 14. Proximal end 30 of fitting 14 defines a female luer connector that can be mated with an appropriate male luer connector to infuse a medication into a patient. The male luer connector may include a proximal needle cannula that can be placed in communication with an evacuated tube. In addition, the male luer connector may include an evacuated tube holder mounted to the male luer connector hub. Alternatively, a male luer connector at the distal end of a conventional prior art syringe can be connected directly to proximal fitting 14 for infusing a medication into the patient. In this instance, a separate male luer cap can be provided for closing proximal fitting 14. Other fittings may be threadedly engaged with proximal fitting 14 in accordance with the specific intended use of collection/infusion set 10. Additionally, proximal connectors of other configurations may be employed to achieve a particular objective. One example of a fitting is a non-patient needle assembly with a male luer hub, a non-patient needle and a non-patient sleeve mounted over the non-patient needle and secured to male luer hub. The non-patient sleeve functions as a valve that permits multiple punctures of evacuated containers.

Needle assembly 16 includes a needle cannula 34, a needle hub 36 and a needle protector 38. Needle cannula 34 has a proximal end 40, a distal end 42 and a lumen 44 extending between the ends. Distal end 42 of needle cannula 34 is beveled to a sharp tip.

Needle hub 36 is molded unitarily from a plastic material such as polycarbonate, polypropylene, polyethylene, acrylic, polystyrene and ABS. Preferably needle hub 36 is molded from a transparent or translucent material to enable observation of blood or other fluid flowing through needle hub 36, such as by solvent bonding or welding. Needle hub 36 includes a proximal end 46, a distal end 48 and a stepped passage 50 extending between the ends. Portions of passage 50 adjacent proximal end 46 are dimensioned to receive distal end 28 of tubing 12. More particularly, distal end 28 of tubing 12 is telescoped into passage 50 of needle hub 36 and is bonded in position adjacent proximal end 46 of needle hub 36. Portions of passage 50 adjacent distal end 48 of needle hub 36 are dimensioned for slidable receipt of proximal end 40 of needle cannula 34.

External portions of needle hub 36 adjacent distal end 48 define a small diameter cylindrical tip 52. An intermediate diameter cylindrical spring mounting section 54 extends proximally from small diameter cylindrical tip 52, and a larger diameter cylindrical flange 56 extends outwardly at proximal end of spring mounting section 54. Flange 56 defines a limit for proximal movement of spring 18 on needle hub 36 and a limit for distal movement of needle hub 36 relative to front barrel 20.

An actuator arm 60 is cantilevered to extend outwardly and distally from proximal end 46 of needle hub 36. The outward projection enables actuator arm 60 to function as a key that ensures and maintains a specific rotational orientation of needle hub 36 relative to front and rear barrels 20 and 22. Additionally, actuator arm 60 and beveled tip 42 of needle cannula 34 are aligned symmetrically with one another. More particularly, a plane passing symmetrically through actuator arm 60 would also bisect the ellipse defined by beveled tip 42. Alternatively, actuator arm 60 may be located on any side of needle hub 36.

Actuator arm 60 includes a distal end 62 that is located proximally of flange 56. Thus, flange 56 does not impede inward deflection of actuator arm 60. Portions of actuator arm 60 proximally of distal end 62 define an actuator button 64 that projects radially outwardly on actuator arm 60. The proximal end of actuator button 64 defines a locking edge 66 which is undercut relative to remaining portions of actuator arm 60 and oriented at an acute angle to the axis of needle hub 36. A bottom stabilizing rib 67 extends axially along needle hub 36. If needed, more than one stabilizing rib may be used.

Needle protector 38 is a rigid cylindrical tube that provides the ability to extend past the projecting length of needle cannula 34 from distal end 72 of front barrel 20. As shown in FIG. 3, needle protector 38 attaches to needle hub 36 and has a length that exceeds the projecting length of needle cannula 34 from needle hub 36. Needle protector 38 defines an inside diameter approximately equal to the outside diameter of distal tip 52 of needle hub 36. Additionally, needle protector 38 defines an outside diameter approximately equal to the outside diameter of spring mounting section 54 of needle hub 36. Thus, as shown most clearly in FIG. 4, needle protector 38 can be telescoped over needle cannula 34 and frictionally retained on distal tip 52 of needle hub 36. Additionally, in this mounted condition, spring mounting section 54 of needle hub 36 and needle protector 38 define a continuous and substantially uniform outside diameter. Alternatively, needle protector 38 may be retained frictionally on distal end 72 of front barrel 20 to further extend past the needle cannula 34.

Spring 18 defines a helical coil with an inside diameter slightly greater than the outside diameter of needle protector 38 and spring mounting section 54 of needle hub 36. Additionally, inside diameter of spring 18 is less than the outside diameter of flange 56 on needle hub 36. Thus, flange 56 defines a limit to the range of telescoping movement of spring 18 over needle assembly 16. The axial length of spring 18 is selected to conform with the desired range of movement of needle assembly 16 relative to front and rear barrels 20 and 22. More particularly, the axial length of spring 18 in its expanded condition exceeds the distance between distal tip 42 of needle cannula 34 and flange 56 on needle hub 36.

Front barrel 20 is a unitarily molded plastic structure with opposite proximal and distal ends 70 and 72, and a passage 74 extending between the ends. Portions of passage 74 near distal end 72 define an inwardly extending annular distal flange 76 with an inside diameter less than the outside diameter of spring 18. Thus, distal flange 76 defines a distal stop for spring 18 and enables spring 18 to be compressed within front barrel 20. Passage 74 further has an annular step 78 proximally of distal flange 76. Step 78 defines an inside diameter less than the outside diameter of flange 56 on needle hub 36. Thus, step 78 defines a fixed limit for distal movement of needle hub 36 in front barrel 20. Step 78 is spaced from distal flange 76 by a distance substantially equal to the compressed length of spring 18. Thus, the section of passage 74 between distal flange 76 and step 78 effectively defines a spring housing. Passage 74 is defined further by an annular locking rib 80 near proximal end 70. Locking rib 80 permits locked engagement of front and rear barrels 20 and 22 as explained herein.

The outer circumferential surface of front barrel 20 is defined by an annular wing-mounting undercut 82 near distal end 72. Annular undercut 82 is provided with detents 83 for positioning wings 24 in a fixed rotational orientation on front barrel 20. Undercut 82 of front barrel 20 may have a dampening agent injection port 85 for injecting a dampening agent into passage 74. Port 85 then is covered by wings 24.

Portions of the outer surface of front barrel 20 proximally of annular undercut 82 are flared outwardly to larger cross-sectional dimensions. However, the outer circumferential surface is necked down to define a reduced diameter portion that extends through at least approximately 270° around the circumference of front barrel 20. Thus, front barrel 20 has a distal major diameter portion 84, a proximal major diameter portion 86 and a minor diameter portion 88 therebetween. Minor diameter portion 88 of front barrel 20 includes an actuator aperture 90 extending therethrough and communicating with passage 74. Actuating aperture 90 is dimensioned and configured to receive actuating button 64 and includes a locking edge 92 configured for engaging locking edge 66 of actuating button 64. Actuating aperture 90 is positioned angularly at a central location on minor diameter portion 88, and is aligned with projection 83 on undercut 82 to define a visually apparent top for an otherwise substantially symmetrical front barrel 20. Step 78 is spaced from actuating aperture 90 by a distance equal to or slightly greater than the axial distance between distal end 62 of actuator arm 60 and the distal face of flange 56. Thus, actuator button 64 is engaged in actuating aperture 90 when flange 56 of needle hub 36 substantially abuts step 78 of front barrel 20. Additionally, the internal cross-sectional dimension of passage 78 adjacent to and proximal of locking edge 92 is substantially equal to or slightly less than the cross-sectional dimension of actuating arm 60 adjacent to and proximally of locking edge 66. Hence, locked engagement is assured between locking edges 66 and 92 when needle hub 36 is moved distally in front barrel 20 a sufficient distance for flange 56 to substantially abut step 78.

Rear barrel 22 also is a substantially tubular structure with a proximal end 94, a distal end 96 and a passage 98 extending between the ends. Exterior portions of outer barrel 22 adjacent distal end 96 define an annular locking bead or ring 100. Locking bead 100 is configured for snapped locked engagement with annular locking rib 80 in passage 74 of front barrel 20 to engage front and rear barrels 20 and 22 with one another. The engagement of front and rear barrels 20 and 22 can be made more permanent by adhesive bonding, welding, or by increasing the interference between annular locking rib 80 and locking bead 100. Alternately, front barrel 20 and rear barrel 22 may be connected by threaded engagement where one of front or rear barrels 20 and 22 has external threads and the other of front and rear barrel 20 and 22 has internal threads. Thread pitch and location would be chosen to enable alignment of top and bottom axially extending channels 104 and 106.

Proximal portions of passage 98 through rear barrel 22 are characterized by an inwardly extending proximal flange 102. Proximal flange 102 has an inside diameter less than the outside diameter of flange 56 on needle hub 36. Thus, proximal flange 102 limits proximal movement of needle hub 36 in rear barrel 22.

Passage 98 of rear barrel 22 is characterized further by top and bottom axially extending channels 104 and 106 respectively. Top channel 104 is aligned with actuating aperture 90 and is dimensioned to slidably receive actuating arm 60 of needle hub 36. Bottom channel 106 is dimensioned to slidably receive bottom stabilizing rib 67 of needle hub 36. Portions of rear barrel 22 surrounding bottom channel 106 project proximally beyond top channel 104. As a result, a greater axial length is provided for slidably receiving and supporting bottom stabilizing rib 67 of needle hub 36. This additional support for bottom stabilizing rib 67 achieves a more desirable bearing ratio between the cross-sectional and axial dimensions for slidable engagement between needle hub 36 and barrels 20 and 22. Accordingly, a more precise axial movement is achieved with less transverse shifting of needle hub 36. The more precise axial movement enabled by the proximal extension surrounding bottom channel 106 substantially reduces splattering of residual fluid in needle cannula 34 during retraction.

Rear barrel 22 is characterized further by resiliently deflectable locking fingers 108 that are cantilevered proximally and inwardly from opposed locations on rear barrel 22 that are spaced from top and bottom channels 104 and 106 by approximately 90°. Each locking finger 108 includes a proximal end 110 that is spaced from proximal stop flange 102 by a distance equal to or slightly greater than the axial thickness of flange 56 on needle hub 36. Hence, flange 56 can be trapped between the distal surface of stop flange 102 and locking figures 108 as explained below. Proximal ends 108 of locking figures 110 are spaced from one another by a distance less than the diameter of flange 56 on needle hub 36.

Wings 24 are molded unitarily from an elastic material such as polyolefin, polyvinyl chloride or other such elastomeric polymers. Wings 24 include flexible side panels 112 and 114 and a tubular mount 116. Tubular mount 116 includes an interior passage 118 that is dimensioned for snug engagement over under cut 82 on front barrel 20. Additionally, mount 16 is formed with top and bottom notches 120 and 122 that are dimensioned to engage with detents 83 on front barrel 20 to ensure a preferred rotational orientation of wings 24. Notches 120 and 122 are symmetrical about a plane that is perpendicular to panels 112 and 114. Preferably, panels 112 and 114 are molded with a top surface that is relatively smooth. However, the top surface of panel 112 includes a pair of arcuate projections 124 at portions remote from tubular mount 116. The top surface of panel 114 includes a pair of arcuate recesses 126 that are dimensioned, disposed and configured to receive projections 124 on panel 112 when panels 112 and 114 are folded so that the top surfaces thereof are in face-to-face engagement with one another. The interengagement of projections 124 with recesses 126 ensures that folded panels 112 and 114 function as a handle without slipping relative to one another. The bottom surfaces of panels 112 and 114 are provided with a plurality of tactile bumps 132. Bumps 132 facilitate gripping of folded panels 112 and 114 between a thumb and forefinger of the user. The hinged movement of panels 112 and 114 about tubular mount 116 is facilitated by thinned regions at the connection of panels 112 and 114 with tubular mount 116. The color of the wings 24 preferably designates the gauge of needle cannula 34. Alternate embodiments where wings 24 have only one side panel 112 or 114 are contemplated to provide an alternate means to manipulate the needle assembly by the user.

Fluid collection set 10 is assembled by first mounting proximal end 40 of needle cannula 34 into passage 50 adjacent distal end 48 of needle hub 36. Needle cannula 34 may be secured in this position by an adhesive, such as a heat curable or ultraviolet cured epoxy. As noted above, the orientation of the bevel that defines distal tip 42 of needle cannula 34 is important. Thus, needle cannula 34 is oriented such that the bevel at distal end 42 of needle cannula 34 and wings 126 arm 60 of needle hub 36 are symmetrical about a common plane. Orientation of wings 24 to distal end 42 of cannula 34 is guaranteed by relative orientation of actuator arm 60 and needle hub 36 with respect to front and rear barrels 20 and 22. Needle assembly 16 is completed by telescoping protector 38 over needle cannula 34 sufficiently for frictional engagement on distal tip 52 of needle hub 36. Alternately, protector 38 can be telescoped over needle cannula 34 by fictional engagement with front barrel 20.

Distal end 28 of tubing 12 then is secured in proximal end 46 of needle hub 36. Tubing 12 may be secured in this position by solvent bonding, adhesive bonding or welding.

Assembly continues by telescoping spring 18 over needle protector 38 and over spring mounting section 54 of needle hub 36. Needle assembly 16 and spring 18 then are aligned and telescoped in a distal direction into front barrel 20. This insertion requires actuator arm 60 and stabilizing rib 67 to align with channels 104 and 106. Movement of needle hub 36 into front barrel 20 causes needle protector 38 to advance through and beyond distal end 72 of front barrel 20. Additionally, actuator arm 60 is depressed sufficiently to clear portions of passage 74 immediately proximally of actuating aperture 90. This distal movement causes spring 18 to collapse between distal flange 76 on front barrel 20 and flange 56 on needle hub 36. As flange 56 of needle hub 36 approaches step 78 of front barrel 20, actuator button 64 aligns with actuating aperture 90. Thus, actuator arm 60 resiliently returns toward an undeflected condition and locking edge 66 of actuator button 64 engages locking edge 92 of actuating aperture 90. As a result, needle assembly 16 is locked in its distal position in front barrel 20 with spring 18 secured in a compressed condition with significant stored energy. Wing 24 then is mounted over distal end 72 of front barrel 20. Notches 120 and 122 of wing 24 are aligned with detents 83 on front barrel 20. Thus, a snug fit of mount 116 of wing 24 is achieved with undercut 82 and detents 83 to hold wing 24 on front barrel 20 and to prevent rotation. In this mounted condition, panels 112 and 114 of wing 24 define a plane extending substantially normal to the plane of symmetry defined by the bevel at distal tip 42 of needle cannula 34 and actuator arm 60 of needle hub 36. Assembly continues by threading proximal end 26 of tubing 12 through rear barrel 22. Sufficient distal movement of rear barrel 22 along tubing 12 enables locked engagement of distal end 96 of rear barrel 22 within proximal end 70 of front barrel 20. Fitting 14 then can be secured to proximal end 26 of tubing 12.

When a viscous dampening agent is used, the passage 74 of front barrel 20, the spring mounting section 54 of needle hub 36, and the distal surface of the flange 56 on needle hub 36 define a chamber that constrains the preferred location of the dampening agent. An injection port 85 located within the sidewall of front barrel 20 is preferred for dispensing the viscous dampening agent into the chamber. Preferably, the dampening agent can be injected through a dispensing cannula that has a distal end shaped to fit within injection port 85. It is also contemplated that the dampening agent can be applied to passage 74, spring 18, needle hub 36, or any of the three components prior to assembly to produce an alteration to retraction speed or velocity.

The viscous dampening agent may be a silicone that functions to dampen the velocity of needle hub 36 relative to front barrel 20 and rear barrel 22. The viscous dampening agent creates a resistance to slow the retraction of needle hub 36 and needle cannula 34. A preferred dampening agent is a thixotropic gel, similar to the type of gel used as a separator gel in blood collection tubes. A thixotropic gel used as a dampening agent provides unique properties relative to spring 18. In particular, the thixotropic gel exhibits the ability to temporarily and elastically bond adjacent coils of spring 18 together. Initiation of retraction releases the stored energy of spring 18, and permits spring 18 to expand. The thixotropic gel creates resistance similar to silicone, and hence dampens the velocity of hub 36 and needle cannula 34. However, unlike conventional silicone, the temporary bonding between adjacent coils achieved by the thixotropic gel provides a slower initial acceleration. The slower initial acceleration results in a significant reduction in splatter during retraction of needle cannula 34.

Injection port 85 can be positioned on undercut 82 and can be sealed by placing wing 24 on and covering injection port 85, thereby constraining the dampening agent to that portion of the spring 18 near the injection port 85. Alternatively, it is understood that a dampening agent can be located at surfaces in slidable engagement between the needle hub 36 and front and rear barrels 20 and 22. This would produce a viscous shearing boundary layer that also can alter the velocity and acceleration of needle hub 36 retraction.

Fluid collection or infusion set 10 is used by folding panels 112 and 114 of wing 24 toward one another and into face-to-face engagement so that projections 118 on upper surface of panel 112 are received in recesses 120 on the upper surface on panel 114 to prevent shifting of panels 112 and 114. Tactile bumps 132 on the bottom surfaces of panels 112 and 114 then can be held securely in face-to-face engagement between a thumb and forefinger. Needle protector 38 then is separated from needle hub 36 to expose needle cannula 34. In this condition, the plane defined by abutting surfaces of panels 12 and 14 of wing 24 will lie on the plane of symmetry of beveled distal tip 42 of needle cannula 34. The health care worker then guides beveled distal tip 42 of needle cannula 34 into a targeted location on the patient and employs fitting 14 at proximal end 26 of tubing 12 for connection to an evacuated container or a source of fluid that will be infused into the patient. Upon completion of the medical procedure, the health care worker depresses actuator button 64 to withdraw needle cannula 34 proximally where front barrel 20 entirely encloses needle cannula 24. In this regard, actuator button lies within the cross-sectionally reduced portion 88 of front barrel 20, and hence is not susceptible to inadvertent actuation. However, the configuration of cross-sectionally reduced portion 88 is dimensioned to receive a tip of a forefinger that is intentionally directed toward actuator button 64. Furthermore, the necked-down shape of front barrel 20 adjacent actuating aperture 90 provides a clear visual cue for the intended location of digital forces for depressing actuator button 64.

Inwardly directed forces on actuator button 64 cause locking edge 66 of actuator button 64 to disengage from locking edge 92 of actuating aperture 90. Hence, spring 18 is permitted to expand and propels needle assembly 16 proximally. Proximal movement of needle assembly 16 terminates when flange 56 abuts proximal stop flange 102 of rear barrel 22. In this position, the entirety of needle cannula 38 is disposed safely within front and rear barrels 20 and 22. The proximal movement of needle assembly 16 is guided axially by engagement of bottom stabilizing rib 67 in bottom channel 106. Additionally, actuator button 64 travels in top channel 104 and biases needle assembly 16 toward bottom channel 106, including portions of bottom channel 106 in proximal extension of rear barrel 22. Hence, an effective bearing ratio is maintained to achieve merely axial movement, with a reduced probability of splatter as needle cannula 34 is accelerated proximally due to forces exerted by spring 38.

As flange 56 of needle hub 36 approaches proximal stop 102, flange 56 also will engage locking fingers 108. Rearward movement of flange 56 causes an outward deflection of locking fingers 108. However, when flange 56 abuts proximal stop 102, locking fingers 108 resiliently return toward an undeflected condition and engage the distal face of flange 56. Hence, a return movement of needle assembly 16 is prevented. Furthermore, the inwardly aligned orientation of locking fingers 108 substantially impedes any intentional outward deflection of locking fingers 108 that would permit a re-exposure of needle cannula 38. Hence, reuse of needle cannula 38 can be achieved only by a substantially complete destruction of the locking fingers in rear barrel 22.

An alternate embodiment of the wings is identified by the numeral 224 in FIGS. 18-21. Wings 224 are similar to wings 24, and include panels 212 and 214 that extend from a tubular mount 216. However, wings 224 further have an actuating arm 228 extending proximally from tubular mount 216 and ending with a projection 230 that is disposed and dimensioned to register with actuating aperture 90 in front barrel 20 and with actuator button 64 of hub 36. Upper surfaces of actuating arm 228 are wider than projection 230 and are provided with tactile bumps 232 projecting therefrom. Actuating arm 228 is flexible and provides the user an improved ability to indirectly depress actuator button 64 by depressing actuating arm 228 through aperture 90 and into actuating button 64.

Figure 22:
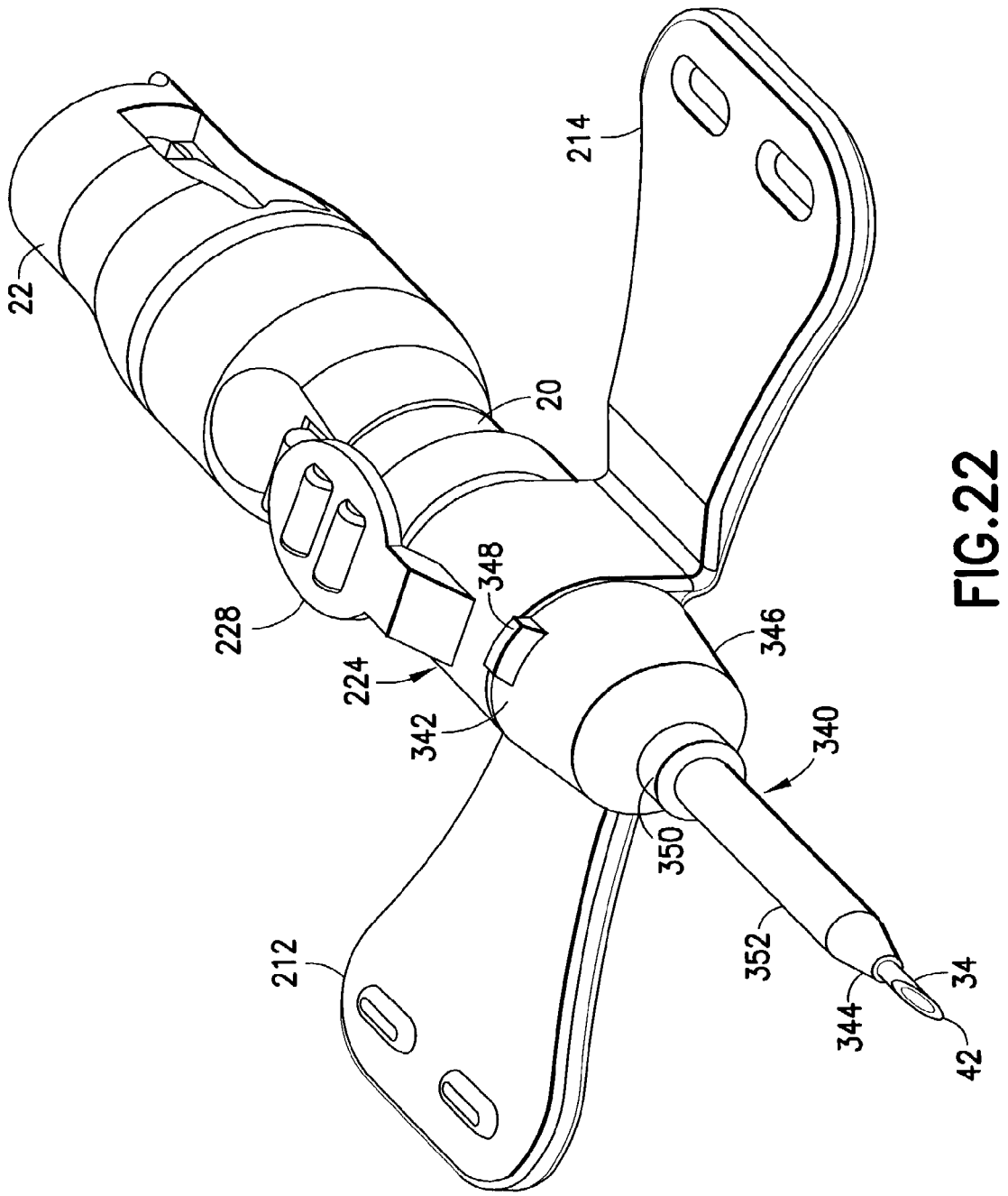
FIG. 22 is a perspective view of the apparatus used with a catheter.
Figure 23:
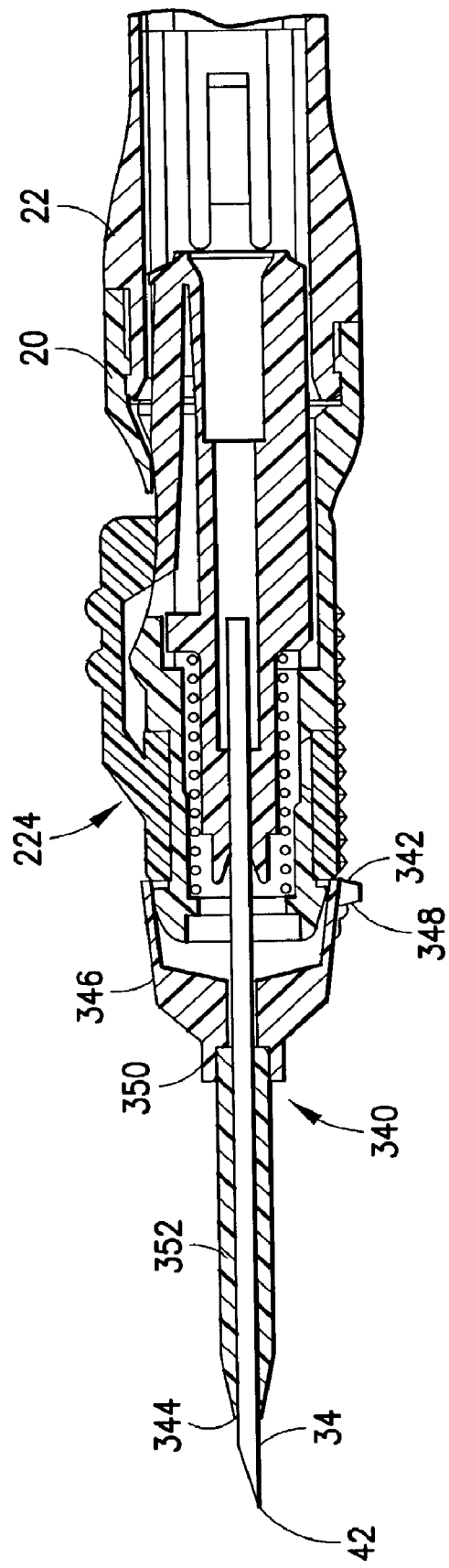
FIG. 23 is a longitudinal cross-sectional view of the retractable apparatus of FIG. 22.

The preceding embodiments relate to fluid collection sets or fluid infusion sets. FIGS. 22-24 illustrate an embodiment of the invention that relates to a catheter. In particular, the embodiment of FIGS. 22-24 includes a needle assembly 16 that may be substantially identical to the needle assembly described and illustrated above. Needle assembly 16 is used with a coil spring 38 and is disposed for axial movement between front and rear barrels 20 and 22 as described above. In this embodiment, however, it is unnecessary to provide flexible plastic tubing or a proximal fitting. Rather, the embodiment of FIGS. 22-24 includes a catheter 340 with a proximal end 342 and a distal end 344. Sections of catheter 340 adjacent proximal end 342 define a frustoconically generated mounting section 346 formed from a rigid plastic and dimensioned for frictional engagement over distal end 72 of front barrel 20. Mounting section 346 is characterized by Luer lugs 348 extending outwardly thereon. Lugs 348 can be engaged threadedly with a Luer collar of a syringe or other medical device. Mounting section 346 includes a generally cylindrical distal end 350. Catheter 340 further includes a generally tubular insertion section 352 inserted into cylindrical distal end 350 of mounting section 346 and secured therein by adhesive bonding, welding or the like. Insertion section 352 is formed from a material that is more pliable than mounting section 346, such as polyurethane or silicone. Insertion section 352 has a cylindrical passage dimensioned for telescoping over needle cannula 34. The outer surface of insertion section 352 is cylindrically generated. However, portions of insertion section 352 at distal end 344 of catheter 340 are conically tapered. Insertion section 352 defines a length selected so that distal end 344 of catheter 340 is disposed proximally of distal end 342 of needle cannula 34. A needle protector (not shown) may be telescoped over both needle cannula 34 and insertion section 352 of catheter 340 and may be frictionally retained on cylindrical distal end 350 of mounting section 346. The needle protector extends sufficiently to cover distal tip 42 of needle cannula 34.

The embodiment of FIGS. 22-24 is used by first separating the protective cap to expose distal end 42 of needle cannula 34 and insertion section 352 of catheter 340. Distal end 42 and needle cannula 34 then is guided into a targeted location on a patient and guides distal end 344 of catheter 340 into the patient. After the appropriate location has been accessed, the user exerts pressure on lugs 348 while pulling wing panels 112 and 114 proximally. Insertion section 352 of catheter 340 is squeezed closed as needle cannula 34 is withdrawn. This may be achieved with a hemostat or similar device. The Luer collar of a syringe then may be threadedly engaged with Luer lugs 348 on mounting section 346 of catheter 340 for delivering a liquid medication or other solution into a patient.

What is claimed is:

1. A retractable safety needle comprising:
   a needle hub having proximal and distal ends and a passage extending between said ends;
   a needle cannula having a proximal end, a distal end and a lumen extending therebetween, said needle cannula being securely mounted in said passage;
   a resiliently deflectable actuator arm extending from said needle hub, an actuator button being formed on said actuator arm;
   a barrel having a proximal end, a distal end and a passage extending between said ends, said needle hub being disposed in said passage of said barrel such that said needle hub, said needle cannula and said actuator arm are movable relative to said barrel from a distal position where said needle cannula projects distally beyond said barrel and a proximal position wherein said distal end of said needle cannula is disposed in said barrel, said barrel having an actuating opening extending therethrough, said actuator button engaging portions of said barrel adjacent said actuating opening when said needle hub is in said distal position, said actuator button being resiliently deflectable out of engagement with said actuating opening;
   a spring having a proximal and a distal end disposed in said barrel for propelling said needle hub to said proximal position when said actuator button is deflected out of said actuating opening;
   at least one flange extending from said barrel to limit proximal movement of said needle hub;
   at least one flange extending from said needle hub that limits proximal movement of said needle hub and contacts said proximal end of said spring;
   a first axially extending channel located within said passage of said barrel, said channel adapted for engaging said hub and limiting the movement of said hub to axial movement; and
   at least one resiliently deflectable locking finger extending from said barrel.

2. The retractable safety needle of claim 1, wherein said at least one locking finger being configured to lockingly engage said needle hub when said needle hub reaches said proximal position.

3. The retractable safety needle of claim 1, wherein said at least one locking finger being configured to deflect to allow said needle hub to reach said proximal position and lockingly engage said needle hub when said needle hub reaches said proximal position.

4. The retractable safety needle of claim 1, wherein said at least one locking finger being configured to lockingly engage said needle hub at a location other than said actuator arm to prevent re-exposure of said needle cannula when said needle hub reaches said proximal position.

5. The retractable safety needle of claim 1, said needle hub further comprising a needle hub flange, wherein said at least one locking finger being configured to lockingly engage said needle hub flange to prevent re-exposure of said needle cannula when said needle hub reaches said proximal position.

6. A retractable safety needle comprising:
   a needle hub having proximal and distal ends and a passage extending between said ends;
   a needle cannula having a proximal end, a distal end and a lumen extending therebetween, said needle cannula being securely mounted in said passage;
   a resiliently deflectable actuator arm extending from said needle hub, an actuator button being formed on said actuator arm;

a barrel assembly comprising a front barrel having a proximal end and a distal end, a rear barrel having a proximal end and a distal end, and said barrel assembly having a passage extending between said ends, said needle hub being disposed in said passage of said barrel assembly such that said needle hub, said needle cannula and said actuator arm are movable relative to said barrel assembly from a distal position where said needle cannula projects distally beyond said barrel assembly and a proximal position where said distal end of said needle cannula is disposed in said barrel assembly, said barrel assembly having an actuating opening extending therethrough, said actuator button engaging portions of said barrel assembly adjacent said actuating opening when said needle hub is in said distal position, said actuator button being resiliently deflectable out of engagement with said actuating opening;

a first axially extending channel located within said passage of said barrel, said channel adapted for engaging said hub and limiting the movement of said hub to axial movement;

at least one flange extending from said needle hub that limits proximal movement of said needle hub; and a spring extending between said barrel assembly and said flange of said needle hub for propelling said needle hub to said proximal position when said actuator button is deflected out of said actuating opening.

7. The retractable safety needle of claim 6, wherein said actuating opening extends through said front barrel.

8. The retractable safety needle of claim 6, further comprising a locking rib positioned towards said proximal end of said front barrel and an annular locking ring positioned towards said distal end of said rear barrel for the mating of said front barrel and rear barrel.

9. The retractable safety needle of claim 6, wherein said front barrel is formed from at least one of a transparent and translucent material and wherein said needle hub is formed from at least one of a transparent and translucent material, to permit an indication when venous blood reaches the inside of said needle hub.

10. A retractable safety needle comprising:
a needle hub;
a needle cannula mounted in a passage in said needle hub;
a resiliently deflectable actuator arm extending from said needle hub, an actuator button being formed on said actuator arm;
a barrel having a proximal end, a distal end and a passage extending between said ends, said needle hub being disposed in said passage of said barrel such that said needle hub, said needle cannula and said actuator arm are movable relative to said barrel from a distal position where said needle cannula projects distally beyond said barrel and a proximal position where said distal end of said needle cannula is disposed in said barrel, said barrel having an actuating opening extending therethrough, said actuator button engaging portions of said barrel adjacent said actuating opening when said needle hub is in said distal position, said actuator button being resiliently deflectable out of engagement with said actuating opening;
a first axially extending channel located within said passage of said barrel, said channel adapted for engaging said hub and limiting the movement of said hub to axial movement;
at least one flange extending from said needle hub that limits proximal movement of said needle hub; and
a spring extending between said barrel and said flange on said needle hub for propelling said needle hub to said proximal position when said actuator button is deflected out of said actuating opening.

11. The retractable safety needle of claim 10, said barrel further comprising a second axially extending channel.

12. The retractable safety needle of claim 11, wherein said stabilizing rib travels in at least one of said first channel or said second channel.

13. The retractable safety needle of claim 11, wherein said second channel extends proximally beyond said first channel.

14. The retractable needle assembly of claim 11, wherein during movement from said distal position to said proximal position, said actuator button biases said needle hub towards at least one of said first channel and said second channel.

15. The retractable safety needle of claim 10, wherein said needle hub further comprises a stabilizing rib.

16. The retractable safety needle of claim 15, wherein said stabilizing rib travels in said first channel.

17. The retractable safety needle of claim 10, wherein said actuator button travels in said first channel.

18. The retractable needle assembly of claim 10, said needle hub further comprising a key, wherein said key maintains a predetermined rotational orientation of the needle hub with respect to the barrel.

19. A retractable safety needle comprising:
a needle hub having a needle hub flange, wherein said needle hub flange is spaced apart from a distal end of the needle hub and a resiliently deflectable actuator arm extending from said needle hub, an actuator button being formed on said actuator arm;
a needle cannula being securely mounted in a passage in said needle hub;
a barrel having a proximal end, a distal end and a passage extending between said ends, said needle hub being disposed in said passage of said barrel such that said needle hub, said needle cannula and said actuator arm are movable relative to said barrel from a distal position where said needle cannula projects distally beyond said barrel and a proximal position where said distal end of said needle cannula is disposed in said barrel, said barrel having an actuating opening extending therethrough, said actuator button engaging portions of said barrel adjacent said actuating opening when said needle hub is in said distal position, said actuator button being resiliently deflectable out of engagement with said actuating opening;
at least one resiliently deflectable locking finger extending from said barrel; and
a spring disposed in said barrel and contacting said needle hub flange for propelling said needle hub to said proximal position when said actuator button is deflected out of said actuating opening, wherein said needle hub flange interacts with said barrel to limit proximal movement of said needle hub.

20. The retractable safety needle of claim 19, wherein said needle hub further comprises a spring mounting section.

21. The retractable safety needle of claim 20, wherein said spring mounting section is positioned distally from said actuator arm.

22. The retractable safety needle of claim 20, wherein said spring is telescoped over said spring mounting section.

23. The retractable safety needle of claim 19, wherein said needle hub further comprises a chamber in fluid communication with a proximal end of said needle cannula.

* * * * *